US010041036B2

(12) United States Patent
Yoder et al.

(10) Patent No.: US 10,041,036 B2
(45) Date of Patent: *Aug. 7, 2018

(54) ISOLATION, EXPANSION AND USE OF CLONOGENIC ENDOTHELIAL PROGENITOR CELLS

(71) Applicant: Indiana University Research and Technology Corporation, Indianapolis, IN (US)

(72) Inventors: Mervin C. Yoder, Indianapolis, IN (US); David A. Ingram, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/985,908

(22) Filed: Dec. 31, 2015

(65) Prior Publication Data
US 2016/0168533 A1 Jun. 16, 2016

Related U.S. Application Data

(63) Continuation of application No. 11/055,182, filed on Feb. 9, 2005, now abandoned.

(60) Provisional application No. 60/543,114, filed on Feb. 9, 2004, provisional application No. 60/573,052, filed on May 24, 2004, provisional application No. 60/637,095, filed on Dec. 17, 2004.

(51) Int. Cl.
*C12N 5/00* (2006.01)
*C12N 5/0789* (2010.01)
*C12N 5/071* (2010.01)
*G01N 33/50* (2006.01)
*G01N 33/569* (2006.01)
*A61K 35/12* (2015.01)

(52) U.S. Cl.
CPC ......... *C12N 5/0068* (2013.01); *C12N 5/0647* (2013.01); *C12N 5/0692* (2013.01); *G01N 33/5005* (2013.01); *G01N 33/56966* (2013.01); *A61K 2035/124* (2013.01); *C12N 2501/125* (2013.01); *C12N 2501/145* (2013.01); *C12N 2501/22* (2013.01); *C12N 2501/26* (2013.01); *C12N 2502/28* (2013.01); *C12N 2533/54* (2013.01); *C12N 2533/90* (2013.01); *G01N 2333/70589* (2013.01); *G01N 2333/70596* (2013.01)

(58) Field of Classification Search
CPC ............... C12N 5/0692; C12N 5/0647; C12N 2502/28; C12N 5/069; C12N 2330/10; C12N 5/0607; C12N 2506/11; C12N 5/0634; C12N 6/692; C12N 5/0068; A61L 27/3808; A61L 27/3834; A61L 27/3633; G01N 33/5064
See application file for complete search history.

(56) References Cited

U.S. PATENT DOCUMENTS

| 7,101,707 | B2 | 9/2006 | Castellon |
| 2002/0037278 | A1 | 3/2002 | Ueno et al. |
| 2004/0009589 | A1 | 1/2004 | Levenberg et al. |
| 2006/0034813 | A1* | 2/2006 | Herder ............... C07K 14/755 |
| | | | 424/93.21 |

FOREIGN PATENT DOCUMENTS

| WO | 0036090 A | 6/2000 |
| WO | 03038048 A | 5/2003 |

OTHER PUBLICATIONS

Ingram et al Blood, (Nov. 16, 2003) vol. 102, No. 11, pp. 532a.*
Bompais et al Blood Apr. 1, 2004; 103(7): 2577-84. online publication Nov. 20, 2003.*
Herder et al Arterioscler Thromb Vasc Biol. 2003; 23(12):2266-72. electronic publication date Oct. 9, 2003.*
Eggermann et al Cardiovascular Research 58, 2003, 478-486, I.*
Peichev et al Blood, 2000, 95, 952-958.*
Pelosi et al Blood. 2002; 100(9): 3203-8, IDS).*
Murohara et al J Clinical Invest. 2000; 105(11): 1527-36.*
Kang et al British Journal of Haematology, 2001, 113, 962-969.*
Yoo et al Stem Cells 2003; 21: 228-235.*
Case et al (PNAS, 1999, 96, 2988-2993).*
Lin et al The Journal of Clinical Investigation, 105, 71-77 (Year: 2000).*
Mutein et al Tissue Antigens , 50: 449-458 (Year: 1997).*
Aoki et al., "Functional endothelial progenitor cells differentiate from human umbilical cord blood mononuclear cells isolated by a novel cell filtration method," Blood, vol. 102, No. 11, p. 96Ia (2003).
Bompais et al., "Human endothelial cells derived from circulating progenitors display specific functional properties compared with mature vessel wall endothelial cells," Blood [Online],Retrieved from Internet at <www.bloodjournal.orglcgilreprint12003-0S-277Ovl>.

(Continued)

Primary Examiner — Anoop K Singh
(74) Attorney, Agent, or Firm — Stinson Leonard Street LLP

(57) ABSTRACT

A hierarchy of endothelial colony forming cells (EPCs) was identified from mammalian cord blood, umbilical vein and aorta. A newly isolated cell named high proliferative potential-endothelial colony forming cell (HPP-ECFC) was isolated and characterized. Single cell assays were developed that test the proliferative and clonogenic potential of endothelial cells derived from cord blood, or from HUVECs and HAECs. EPCs were found to reside in vessel walls. Use of a feeder layer of cells derived from high proliferative potential-endothelial colony forming cells (HPP-ECPCS) from human umbilical cord blood, stimulates growth and survival of repopulating hematopoietic stem and progenitor cells. Stimulation of growth and survival was determined by increased numbers of progenitor cells in in vitro cultures and increased levels of human cell engraftment in the NOD/SCID immunodeficient mouse transplant system.

15 Claims, 28 Drawing Sheets

(56) References Cited

OTHER PUBLICATIONS

Eggermann et al., "Endothelial progenitor cell culture and differentiation in vitro: a methodological comparison using human umbilical cord blood," Cardiovascular Research, vol. 58, No. 2 p. 478-486 (2003).
Herder et al., "Sustained expansion and transgene expression of coagulation factor VIIItransduced cord blood-derived endothelial progenitor cells," Arteriosclerosis Thrombosis and Vascular Biology, vol. 23, No. 12, p. 2266-2272 (2003).
Ingram et al., "Identification of a novel hierarchy of endothelial progenitor cells using human peripheral and umbilical cord blood," Blood, vol. 104, No. 9, p. 2752-2760 (2004).
Ingram et al. "Isolation of endothelial outgrowth cells from umbilical cord blood with high clonogenic potential," Blood, vol. 102, No. 11, p. 532a (2003).
Ingram et al., "Vessel wall-derived endothelial cells rapidly proliferate because they contain a complete hierarchy of endothelial progenitor cells," Blood, vol. 105, No. 7, p. 2783-2786 (2004).
Kang et al., "Short-term phytohaemagglutinin-activated mononuclear cells induce endothelial progenitor cells from cord blood CD34+ cells," British Journal of Haematology, vol. 113, No. 4, p. 962-969 (2001).
Lu et al., "In vitro characterization of neural stem cells from human umbilical cord blood," Database Accession No. PREV200300268255 & Abstracts of the Society for Neuroscience, 3200 Annual Meeting of the Society for Neuroscience. Abstract 34.10 (2002).
Antonchuk, J., G. Sauvageau, et al., (2002) "HOXB4-Induced expansion of adult hematopoietic stem cells ex vivo." Cel/I09: 39-45.
Auerbach et al., (2003). Angiogenesis assays: a critical overview. Clin Chem.49:32-40.
Barker et al., (2001) "Survival after transplantation of unrelated donor umbilical cord blood is comparable to that of human leukocyte antigen-matched unrelated bone marrow: results of a matched-pair analysis." Blood 97(1 0): 2957-296I.
Bompais et al., (2004). Human endothelial cells derived from circulating progenitors display specific functional properties compared with mature vessel wall endothelial cells. Blood 103:2577-2584.
Brandt et al. (1999) "Ex vivo expansion of autologous bone marrow CD34(+) cells with porcine microvascular endothelial cells results in a graft capable of rescuing lethally irradiated baboons." Blood94(1): 106-113.
Broxmeyer et al., (1989). Human umbilical cord blood as a potential source of transplantable hematopoietic stem/progenitor cells. Proc Natl Acad Sci V S A 86:3828-3832.
Cairo and Wagner, (1997). Placental and/or umbilical cord blood: an alternative source of hematopoietic stem cells for transplantation. Blood 90:4665-4678.
Choi et al., (1998). A common precursor for hematopoietic and endothelial cells. Development 125:725-732.
Chute et al. (2002) "Ex vivo culture with human brain endothelial cells increases the SCID repopulating capacity of adult human bone marrow." Blood 1 OO( 13): 4433-9.
Gulati et al., (2003). Diverse origin and function of cells with endothelial phenotype obtained from adult human blood. Circ Res 93:1023-1025.
Hristov et al., (2003). Endothelial progenitor cells: mobilization, differentiation, and homing. Arterioscler Thromb Vasc Bio/23:1185-1189.
Hur et al., (2004). Characterization of two types of endothelial progenitor cells and their different contributions to neovasculogenesis. Arterioscler Thromb Vasc Bioi 24:288-293.
Kalka et al., (2000). Transplantation of ex vivo expanded endothelial progenitor cells for therapeutic neovascularization. Proc Nat! Acad Sci USA 97:3422-3427.
Kawamoto et al., (2001). Therapeutic potential of ex vivo expanded endothelial progenitor cells for myocardial ischemia. Circulation 103:634-637.
Lewis et al., (2001) "Umbilical cord blood cells capable of engrafting in primary, secondary, and tertiary xenogeneic hosts are preserved after ex vivo culture in noncontact system." Blood 97(3441-3449).
Lin et al., (2000). Origins of circulating endothelial cells and endothelial outgrowth from blood. J Clin Invest 105:71-77.
McNiece et al., (2002) "Ex vivo expanded cord blood cells provide rapid engraftment in sheep but lack long-term engrafting potential." Exp Hematol30: 612-616.
Murasawa et al., (2002). Constitutive human telomerase reverse transcriptase expression enhances regenerative properties of endothelial progenitor cells. Circulation 106: 1133-1139.
Murohara, T., H. Ikeda, et al. (2000) "Transplanted cord blood-derived endothelial precursor cells against postnatal neovascularization." The Journal of Clinical Investigation 105 (11): 1527-1535.
Peichev et al., (2000) "Expression of VEGFR-2 and AC133 be circulating human CD34(+) cells identifies a population of functional endothelial precursors" Blood 95:952-958.
Rehman et al., (2003). Peripheral blood "endothelial progenitor cells" are derived from monocyte/macrophages and secrete angiogenic growth factors. Circulation 107:1164-1169.
Shi et al., 1998. Evidence for circulating bone marrow-derived endothelial cells. Blood 92:362-367.
Simper et al., (2002). Smooth muscle progenitor cells in human blood. Circulation 106: 1199-1204.
Stevens et al., (2001). NHLBI workshop report: endothelial cell phenotypes in heart, lung, and blood diseases. Am J Physiol Cell Physiol281 :CI422-1433.
Tepper et al., (2002). Human endothelial progenitor cells from type II diabetics exhibit impaired proliferation, adhesion, and incorporation into vascular structures. Circulation 106:2781-2786.
Vasa et al., (2001). Number and migratory activity of circulating endothelial progenitor cells inversely correlate with risk factors for coronary artery disease. Circ Res 89:E 1-7.
Yang et al., (1999). Human endothelial cell life extension by telomerase expression. J Biology Chem. 274:26141-26148.
Yoo et al. (2003) "Adherent cells generated during long-term culture of human umbilical cord blood CD34+ cells have characteristics of endothelial cells and beneficial effect on cord blood ex vivo expansion." Stem Cells 21(2): 228-235.
Venditti et al., Bone Marrow Transplantation, 1999, vol. 24, pp. 1019-1027.
Pelosi et al., Blood, 2002, 100(9), pp. 3203-3208.
McNiece et al., Int. J. Cell Cloning, 1990, May; vol. 8(3), pp. 146-160.
Christenson et al., Biology of Reproduction, 1996, vol. 55, pp. 1397-1404.
Albella, B., J. Segovia, et al., (2003), "Ex vivo expansion of hematopoietic stem cells.", Methods Mol. Biol., vol. 215: pp. 363-373.
Asahara, et al., 1997, Isolation of putative progenitor endothelial cells for angiogenesis, Science, vol. 275, pp. 964-967.
Bailey, et al., 2003, Converging roads: evidence for an adult hemangioblast, Exp. Hematol, vol. 31, pp. 987-993.
Bornhauser, M., 2003, "Ex vivo expansion of umbilical cord blood cells on feeder layers.", Methods Mol. Biol vol. 215: pp. 341-349.
Brandt, et al., 1998, "Bone marrow repopulation by human marrow stem cells after long-term expansion culture on a porcine endothelial cell line.", Experimental Hematology, vol. 26, pp. 950-961.
Devine, et al., 2003, "Clinical application of hematopoietic progenitor cell expansion: current status and future prospects.", Bone Marrow Transplant, vol. 31(4), pp. 241-252.
Heike, et al., 2002, "Ex vivo expansion of hematopoietic stem cell by cytokines.", Biochimica et Biophysica Acta, vol. 1592(3), pp. 313-321.
Kennedy, et al., 1997, A common precursor for primitive erythropoiesis and definitive haematopoiesis, Nature, vol. 386, pp. 488-493.
Kim, et al., 1994, Specific association of human telomerase activity with immortal cells and cancer. Science, vol. 266, pp. 2011-2015.
Lacaud, et al., 2001, Regulation of hemangioblast development. Ann N.Y. Acad. Sci., vol. 938, pp. 96-107.

(56) References Cited

OTHER PUBLICATIONS

Little, et al., 2002, "History of haematopoietic stem-cell transplantation." Nat. Rev. Cancer, vol. 2, pp. 231-238.
McNiece, et al., 2001, "Ex Vivo expansion of hematopoietic progenitor cells and mature cells." Experimental Hematology, vol. 29, pp. 3-11.
Pollok, et al., Differential transduction efficiency of SCID-repopulating cells derived from umbilical cord blood and granulocyte colony-stimulating factor-mobilized peripheral blood. Hum. Gene. Ther., 2001, vol. 12:20952108.
Rafii, et al., 2003, Therapeutic stem and progenitor cell transplantation for organ vascularization and regeneration., Nat. Med., vol. 9, pp. 702-712.
Reya, et al., 2003, "A role for Wnt signalling in self-renewal of hematopoietic stem cells." Nature, vol. 423, pp. 409-414.
Rosler, et al., 2000, "Cocultivation of umbilical cord blood cells with endothelial cells leads to extensive amplification of competent CD34+CD38 cells." Exp. Hematol., vol. 28, pp. 841-852.
Shpall, E. J., R. Quinones, et al. (2002) "Transplantation of ex vivo expanded cord blood." Bioi. Blood & Marrow Transplant 8: 368-376.
Verfaillie, C. (2002) "Hematopoietic stem cells for transplantation." Nat. Immun. 3(4): 314-317.
Willert, et al., 2003, "Wnt proteins are lipid-modified and can act as stem cell growth factors." Nature, vol. 423, pp. 448-452.
Zimmerman, G.A., McIntyre, T.M., and Prescott, S.M. 1985. Thrombin stimulates the adherence of neutrophils to human endothelial cells in vitro. J Clin Invest, vol. 76, pp. 2235-2246.

\* cited by examiner

ISOLATION, EXPANSION AND USE OF CLONOGENIC ENDOTHELIAL PROGENITOR CELLS

CROSS-REFERENCE TO RELATED APPLICATIONS

This application is a continuation of U.S. patent application Ser. No. 11/055,182, filed on Feb. 9, 2005, which claims priority from U.S. Ser. No. 60/543,114 filed Feb. 9, 2004, U.S. Ser. No. 60/573,052 filed May 24, 2004 and U.S. Ser. No. 60/637,095 filed Dec. 17, 2004, the disclosures of which are hereby incorporated by reference in their entireties.

BACKGROUND OF THE INVENTION

Models for stem cell differentiation leading to endothelial and hematopoietic cells are of interest because of the clinical value of stem cells and their progeny. A hallmark of stem and progenitor cells is their ability to proliferate and give rise to functional progeny, and progenitor cells are identified by their clonogenic potential. Methods previously used do not guarantee that single endothelial cells have been isolated and characterized to identify the progenitors.

Endothelial cell proliferation in vivo in normal, mature arterial, venous, and capillary vessels in most mammals is reported to be extremely low, if not nonexistent. In some experimental animals, such as pigs and dogs, radiolabeling studies have demonstrated 0.6-3.0% endothelial cell turnover daily with the dividing cells restricted to focal areas in certain vessels. Whether these dividing endothelial cells are unique and possess proliferative potential that is lacking in other mature endothelium remains undetermined.

In marked contrast, plating of endothelial cells derived from human or animal vessels in vitro is associated initially with brisk endothelial cell proliferation. For example, human umbilical vein endothelial cells (HUVEC) and bovine aortic endothelial cells (BAEC) are two commonly studied models for in vitro analysis of endothelial cell functions. Both HUVEC and BAEC cells proliferate well initially in culture but cell division wanes with time and cells become senescent and fail to divide after 15-20 passages. It is unknown if each endothelial cell derived from the vessels possesses similar proliferative potential or if only some of the cells can divide.

Angiogenesis (neoangiogenesis) is the process of new vessel formation from pre-existing vessels; this is the process reported to give rise to new vessels in adult subjects. Recently, bone marrow derived circulating endothelial progenitor cells (EPCs) have been described and these cells have also been reported to play a role in new vessel formation, at least in some experimental murine ischemic or tumor models. Conflicting evidence indicates that bone marrow derived (EPCs) do not contribute to the endothelial lining of normal arterial, venous, and capillary vessels during development and play only a minor role in neoangiogenesis. A relationship between circulating EPCs and the endothelial cells with proliferative potential that reside in normal vessels is unknown.

Emerging evidence to support the use of EPCs for angiogenic therapies or as biomarkers to assess a patient's cardiovascular disease risk and progression is accumulating and is generating enthusiasm. However, there is no uniform definition of an EPC, which makes interpretation of these studies problematic and prohibits reproduction of cell types suitable for clinical use. Although a hallmark of stem and progenitor cells (e.g. hematopoietic, intestinal, neuronal) is their ability to proliferate and give rise to functional progeny, EPCs are primarily defined by the expression of selected cell surface antigens. Sole dependence on cell surface expression of molecules can be problematic because the expression may vary with the physiologic state of the cell. No assay is reported to assess the proliferative potential (an intrinsic response) in individual endothelial cells or EPCs and thus, no comparative analysis is available.

Previous studies reported that populations of cells termed "endothelial progenitor cells" can be isolated from human umbilical cord blood or adult peripheral blood by culturing either sorted cells expressing the cell surface antigen CD34, or mononuclear cells in defined culture conditions.

Hematopoietic and endothelial progenitor cells share a number of cell surface markers in the developing yolk sac and embryo, and genetic disruption of numerous genes affects both hematopoietic and endothelial cell development. Therefore, these lineages are hypothesized to originate from a common precursor, the hemangioblast. A hierarchy of stem and progenitor cells in hematopoietic cell development is reported. Hematopoietic progenitor cells within the hierarchy are identified by their clonogenic and proliferative potential. Although genetic studies clearly show that the origin of endothelial cells is closely linked to hematopoietic cell development, evidence to support a similar hierarchy of stem and progenitor endothelial cells based on differences in proliferative potential has not been established. That is, a hierarchy of EPCs that can be discriminated by the clonogenic and proliferative potential of individual cells analogous to the hematopoietic cell system has not been reported.

Both hematopoietic stem and progenitor cells (HSC/Ps) are enriched in umbilical cord compared to adult peripheral blood. Cord blood is currently used as an alternative resource of hematopoietic stem cells for transplantation of patients with a variety of hematological disorders and malignancies.

Thousands of patients require a hematopoietic stem cell (HSC) transplant each year. Nearly ⅔ of the patients are unable to find a human leukocyte antigen (HLA) compatible match for the transplant. This is particularly true for many ethnic populations and under-represented minorities. Only ⅓ of Caucasian patients find suitable matched sibling grafts—the most compatible source with the least graft versus host disease (GVHD) complications.

Human umbilical cord blood is known to be an alternative source of HSCs for clinical transplantation. Whether or not the donor cord blood is a full major histocompatible match to the recipient or is mismatched, cord blood cells engraft and repopulate conditioned hosts as a treatment for a variety of congenital or acquired hematologic disorders. Even if the cord blood graft is mismatched with the recipient by two or more loci, the incidence and severity of GVHD is significantly less than that observed for transplantation of a similarly mismatched adult marrow or mobilized peripheral blood graft.

Limitations to a more widespread use of cord blood for transplant include the fact that only a limited number of HSC and progenitor cells are present in a graft. Because most patients do not have a matched sibling donor, most cord blood grafts are transplanted into mismatched recipients. Multiple studies report that the dose of cord blood cells in a graft is critical for patient survival when the graft comes from an unrelated donor. Transplant related mortality is reported as 20% in recipients that obtained a cord blood graft with $>1.7 \times 10^5$ CD34+ cells/kg versus 75% in those receiving fewer CD34+ cells in the graft. Finding a method to effectively expand cord blood HSC ex vivo to increase the number of cells in a graft, would be a major advance for clinical transplantation and would have a significant commercial market.

Approaches to cord blood HSC expansion have not been impressive. In most studies, addition of a variety of growth factors to cord blood mononuclear cells or isolated CD34+ cells has been correlated with increases in total cell numbers, colony forming unit cell (CFC) numbers, and in short-term progenitor cell engraftment in immunodeficient (NOD/SCID) mice or fetal sheep. However, few approaches have been effective in increasing the number of HSC as measured by SCID repopulating cells (SRC) frequency in NOD/SCID mice or long-term engraftment in fetal sheep. The results of using expanded cord blood HSC in human patients have been disappointing.

SUMMARY OF THE INVENTION

A single-cell colony assay was developed to describe a novel hierarchy among mammalian endothelial progenitor cells (EPCs) isolated from peripheral blood and umbilical cord and from endothelial cells isolated from umbilical or adult blood vessels. A distinct population of progenitor cells from human, bovine, porcine and rat biological samples was identified based on clonogenic and proliferative potential.

Endothelial progenitor cells (EPCs) were isolated from adult peripheral and umbilical cord blood and expanded exponentially ex vivo. In contrast, human umbilical vein endothelial cells (HUVECs) or human aortic endothelial cells (HAECs) derived from vessel walls are widely considered to be differentiated, mature endothelial cells (ECs) and are utilized as "controls" for EPC studies. However, similar to adult and cord blood derived EPCs, HUVECs and HAECs derived from vessel walls can be passaged for at least 40 population doublings in vitro. Utilizing a novel single cell deposition assay, which discriminates EPCs based on their proliferative and clonogenic potential, EPCs were found to reside in HUVECs or HAECs. A single cell clonogenic assay was developed to define a novel hierarchy of EPCs based on their proliferative and clonogenic potential. A complete hierarchy of EPCs was identified in HUVECs and HAECs derived from vessel walls and discriminated by their clonogenic and proliferative potential. Diversity of EPCs exists in human vessels and provides a conceptual framework for determining both the origin and function of EPCs in maintaining vessel integrity. EPCs are therefore readily obtained for clinical use e.g. grafts, either from peripheral blood or from biopsies of human vessels.

Isolated endothelial colony forming cells have the following characteristics:

(a) express cell surface antigens that are characteristic of endothelial cells, such as CD31, CD105, CD146, and CD144;

(b) do not express cells surface antigens that are characteristic of hematopoietic cells, such as CD45 and CD14;

(c) ingest acetylated LDL; and (d) form capillary-like tubes in MATRIGEL® (extracellular matrix proteins).

The isolated cells classified as HPP-ECFC also (a) replate into at least secondary colonies of at least 2000 cells when plated from a single cell;

(b) exhibit high proliferation;

(c) proliferate from a single cell; and (d) express high levels of telomerase, at least 34% of that expressed by HeLa cells. HPP-ECFC also display a high nuclear to cytoplasmic ratio that is >0.8, cell diameters <22 microns, and at least $10^7$ progeny derive from a single cell.

A method of isolating endothelial colony cells includes steps of:

(a) culturing cells from a biological sample on supports coated with extracellular matrix proteins;

(b) selecting cells that adhere to the supports and form replatable colonies; and (c) selecting single cells from the colonies.

The biological sample may be mammalian cord blood, or blood vessel. Human, bovine, porcine and rat sources are suitable. A single cell assay for types of endothelial cells includes the steps of:

(a) cell sorting of biological samples using a specific sorting method;

(b) culturing the single sorted cells on extracellular matrix protein under defined conditions; and (c) enumerating specific colony sizes, morphology, and proliferative potential to determine the type of endothelial cell e.g. HPP-ECFC.

A method of enriching for HPP-ECFC includes the steps of:

(a) cell sorting of biological samples using a specific sorting method; and (b) culturing of single sorted cells on extracellular matrix proteins under defined conditions.

A method for expanding hematopoietic stem cells ex vivo, include the steps of:

(a) culturing HPP-ECFC cells on collagen coated solid supports; and (b) expanding hematopoietic stem cells (HSC) by co-culturing with HPP-ECFC cells wherein the HPP-ECFCs are derived from human cord blood cells and the HSC cells are derived from human bone marrow.

A method for improving the percentage of hematopoietic stem cells in a graft in a mammal, includes the step of:

(a) co-culturing human bone marrow cells with cord blood HPP-ECFC to form a product; and (b) transplanting a suitable amount of the product into the mammal wherein the cells are CD45+ cells derived from human bone marrow, and the mammal is a NOD-SCID mouse.

Cord blood high proliferative potential-endothelial colony forming cells (HPP-ECFCs) in co-culture with autologous or unrelated cord blood, mobilized adult peripheral blood, or marrow-derived HSC expands the number of HSC cells and results in an increase in HSC and an increase in HSC repopulating activity leading to higher levels of engraftment in a recipient subject.

Use of a feeder layer of cells derived from high proliferative potential-endothelial colony forming cells (HPP-ECPCs) from human umbilical cord blood, stimulates growth and survival of repopulating hematopoietic stem and progenitor cells. Stimulation of growth and survival was determined by increased numbers of progenitor cells in in vitro culture and increased levels of human cell engraftment in the NOD/SCID immunodeficient mouse transplant system.

BRIEF DESCRIPTION OF THE DRAWINGS

(FIG. 1A) Number of EPC colonies isolated per 20 ml of adult peripheral (AB) and umbilical cord (CB) blood. Results represent the average number of EPC colonies ±SEM of 18 independent experiments for adult donors and 13 independent experiments for cord blood samples. *P<0.0001 by Student paired t test. (FIG. 1B) Time of initial EPC colony appearance after culture initiation from equivalent volumes of adult peripheral (AB) and umbilical cord (CB) blood. Results represent the average number of days before initial EPC colony appearance ±SEM of 18 independent experiments for adult donors and 13 independent experiments for cord blood donors. *P<0.0001 by Student paired t test. (FIG. 1C) Representative low and high power photomicrographs of endothelial cell colonies derived from adult blood. (FIG. 1D) Low and high power photomicrographs of endothelial cell colonies derived from CB. (FIG. 1E) Endothelial cell monolayers derived from adult endothelial cell colonies at low and high power magnification. (FIG. 1F) Endothelial cell monolayers derived from CB endothelial cell colonies at low and high magnification. Scale bar in photomicrographs represents 100 µm (left column FIGS. 1C-1F) and 10 µm (right column FIGS. 1C-1F).

(FIGS. 2A-2B) Immunophenotyping of cell monolayers derived from either adult (FIG. 2A) or cord (FIG. 2B) EPC colonies by fluorescence cytometry. Both cord blood and adult EPC-derived cells express CD31, CD141, CD105, CD 146, CD 144, vWF, and Flk-1, but do not express CD45 and CD 14. Some cord blood and adult cells express CD34, CD133, and CD117. Shown is representative data from 18 independent experiments utilizing different adult cell monolayers and 13 independent experiments using different cord blood cell monolayers with similar results. Isotype controls are overlayed in gray on each histogram for each surface antigen tested. (FIG. 2C) Adult and cord blood EPC-derived endothelial cells incorporate DiI-Ac-LDL (50× magnification). A representative photomicrograph is shown for adult and cord blood EPC-derived endothelial cells, which have taken up DiI-Ac-LDL (red) and also stained with DAPI (blue). Shown is representative data from 18 independent experiments utilizing different adult cell monolayers and 13 independent experiments using different cord blood cell monolayers with similar results. Scale bar in photomicrographs represents 100 µm. (FIG. 2D) Adult and cord blood EPC-derived endothelial cells genetically engineered to express enhanced green fluorescence protein (EGFP) plated in MATRIGEL® (extracellular matrix proteins) for formation of capillary-like structures (50× magnification). Shown is representative data from 18 independent experiments utilizing different adult cell monolayers and 13 independent experiments using different cord blood cell monolayers with similar results. Scale bar in photomicrographs represents 100 µm. (FIG. 2E) Adult and cord blood EPC-derived endothelial cells upregulate the cell surface expression of vascular cell adhesion molecules (VCAM-1) in response to either rhTNF-α or rhIL-1. Shown is representative data from 18 independent experiments utilizing different adult cell monolayers and 13 independent experiments using different cord blood cell monolayers with similar results. The isotype control for VCAM-1 is overlayed in gray on each histogram.

(FIG. 4A) Ex vivo expansion of adult (AB) and cord (CB) blood EPC-derived endothelial cells harvested from mononuclear cells. Black boxes represent total cell number at each passage. Cells uniformly expressed the endothelial cell surface antigens shown above (FIGS. 2A-2B) and not the hematopoietic cell specific antigens, CD45 and CD14 at each passage. A representative growth curve for cord blood and adult EPC-derived endothelial cells is shown. Eleven other cord blood and adult endothelial cell monolayers derived from different donors showed similar growth kinetics. (FIGS. 4B-4C) Population doubling times (PDT) and cumulative population doubling levels (CPDL) of cord (CB) blood and adult (AB) EPC-derived endothelial cells during 60 days of culture. Results represent the average number of PDTs and CPDLs ±SEM of 6 independent experiments. *P<0.01 by Student paired t test. (FIG. 4D) DNA synthesis of cord (CB) blood and adult (AB) EPC-derived endothelial cells. Early passage (1-2) cord blood EPC-derived endothelial cells demonstrate increased DNA synthesis in response to 10% FBS, rhVEGF, and rhbFGF compared to adult cells. Results represent the average of 4 independent experiments using endothelial cells derived from different donors. *P<0.01 by Student's paired t test.

(FIG. 5A) Schematic of single cell assays using endothelial cells derived from either adult or cord EPC colonies. (FIG. 5B) The percentage of single adult (AB) or cord (CB) blood EPC-derived endothelial cells undergoing at least one cell division after 14 days of culture. Results represent the average of 5 independent experiments using single endothelial cells derived from different donors. *P<0.01 by Student's paired t test. (FIG. 5C) Average number of cell progeny derived from a single adult (AB) or cord (CB) blood EPC-derived endothelial cell after 14 days in culture. Results represent the average of 5 independent experiments using single endothelial cells derived from different donors. *P<0.01 by Student's paired t test. (FIG. 5D) Percent of dividing single cells giving rise to a colony with the number of cells in the quantitative ranges shown (HPP, LPP, clusters) (FIG. 5E) Representative photomicrographs (50× magnification) of the different endothelial cell clusters (<50 cells), LPP (about 51-2000 cells), and HPP (about 2000- to >10,000 cells) derived from a single cord blood or adult EPC-derived endothelial cell. Results are representative of 4 other independent experiments utilizing cells from different donors. Scale bar in photomicrographs represents 100 µm. LPP-ECFC (51-2000 cells) and HPP-ECFC (2000>10,000 cells) ranges are approximations.

(FIG. 6A) Percent of the cell progeny derived from a single cord (CB) blood or adult (AB) EPC-derived endothelial cell, which formed secondary colonies or rapidly grew to cell confluence after 7 days of culture in a 24 well tissue culture plate. Results represent the average ±SEM of 4 independent experiments using cells derived from 4 different donors. *P<0.01 by Student's paired t test. (FIG. 6) A representative photomicrograph (50× magnification) of the secondary endothelial cell colonies or confluent cell monolayers derived from the cell progeny of a single plated cord blood derived endothelial cell in a 24 well plate after 7 days in culture. Scale bar in photomicrographs represents 100 µm. (FIG. 6C) Growth kinetics of the cell progeny of 11 single plated endothelial cells isolated from three different cord blood donors in long-term culture. Black boxes represent the total number of cells at each passage. (FIG. 6D) Telomerase activity of 1000 early passage adult (lanes 1-4) and cord (lanes 5-8) blood EPC-derived endothelial cells isolated from different donors. Adult and cord cells were tested at a CPDL of 15. P indicates telomerase activity in 1000 HeLa cells, which were used as a positive control, and N indicates a negative control. The average level of telomerase activity in the adult samples was 4±4% and of the cord blood samples 34±10% of the telomerase activity of the HeLa cells (FIG. 6E) Comparison of telomerase activity of early and late passage adult (FIG. 6A) and cord (FIG. 6C) blood EPC-derived endothelial cells. PD indicates the cumulative population doubling level of the cells tested. P indicates telomerase activity in HeLa cells, which were used as a positive control. N indicates a negative control. Three other experiments utilizing early and late passage cord blood and adult EPC-derived endothelial cells from three different donors showed similar results.

(FIGS. 8A-8C) Immunophenotyping of cell monolayers derived from cord blood EPCs (FIG. 8A) umbilical veins (FIG. 8B) or human aortas (FIG. 8C) by fluorescence cytometry. Cord blood EPC-derived ECs, HUVECs and HAECs express CD31, CD141, CD105, CD146, CD144, vWF, and Flk-1, but do not express CD45 and CD 14. Shown is representative data from 5 independent experiments utilizing 5 different cord blood EC monolayers, 5 different HUVEC samples and 5 different HAEC samples with similar results. Isotype controls are overlayed in white on each histogram for each surface antigen tested.

(FIG. 9A) The percentage of single cord blood (CB) EPC-derived ECs, HUVECs, or HAECs undergoing at least one cell division after 14 days of culture. Results represent the average of five independent experiments using single ECs derived from different donors. (FIG. 9B) percent of dividing single cells in an individual well—See FIG. 5B. Percent of single CB EPC-derived EC, HUVEC, or HAEC giving rise to colonies of cells (as classified) in an individual well after 14 days of culture. *P<0.01 by Student's paired test for comparison of a single CB-derived EC versus either a single HUVEC or HAEC. (FIG. 9C) Representative photomicrographs (50× magnification) of the different EC clusters (<50 cells) or colonies (>50 cells) derived from a single cord blood EPC-derived EC, HUVEC, or HAEC. Results are representative of four other independent experiments utilizing cells from different donors. Scale bar in photomicrographs represents 100 µm. (FIG. 9D) Percent of the cell progeny derived from a single cord blood EPC-derived EC, HUVEC, or HAEC, which formed secondary colonies or rapidly grew to cell confluence after seven days of culture in a 24 well tissue culture plate. Results represent the average ±SEM of 4 independent experiments using cells derived from four different donors. *P<0.01 by Student's paired t test for comparison of a single CB-derived EC versus either a single HUVEC or HAEC. (FIG. 9E) A representative photomicrograph (50× magnification) of the secondary EC colonies or confluent cell monolayers derived from the cell progeny of a single plated cord blood EPC-derived EC, HUVEC, or HAEC in a 24 well plate after seven days in culture. Scale bar in photomicrographs represents 100 µm. (FIG. 9F) Telomerase activity in an HPP-ECFC (HPP) and LPP-ECFC (LPP) colony derived from HUVECs. Pos. indicates telomerase activity in HeLa cells, which were used as a positive control, and Neg. indicates a negative control. Results are representative of four other independent experiments. Similar differences in telomerase activity were observed between HPP-ECFC and LPP-ECFC colonies isolated from cord blood ECs and HAECs.

(FIG. 12B) cultured for 7 days with maximal stimulating concentrations of G-CSF, TPO, SCF, or Flt-3; (FIG. 12C) or co-cultured with cord blood HPP-ECFC for 7 days where the gated cells stain positive for the human CD45 antigen; graphs are representative of 3 independent experiments with similar results.

DETAILED DESCRIPTION OF THE INVENTION

Figure 5A:
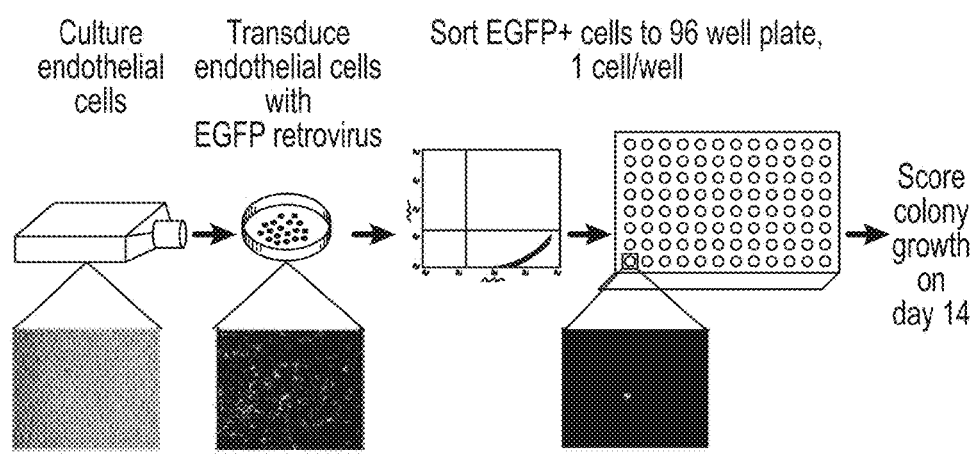
FIGS. 5A-5E. Quantitation of the clonogenic and proliferative potential of single cord blood and adult endothelial cells derived from EPC colonies.

A new endothelial cell progenitor named a high proliferative potential-endothelial colony forming cell (HPP-ECFC) displays high proliferative potential (up to 100 population doublings compared to 20-30 doublings in adult blood EPC. HPP-ECFC were not only isolated from cord blood but from umbilical and adult blood vessels. HPP-ECFC cells can be replated at a single cell level and the majority of cells proliferate with regeneration of at least secondary HPP-ECFCs. (FIG. 7) Unexpectedly, HPP-ECFC colony formations are present in cord blood but not in adult peripheral blood (FIG. 5D). Further, monolayers of cord blood endothelial cells derived from HPP-ECFCs demonstrate a 2.5-fold decrease in population doubling times (PDT) and at least a 2-fold increase in cumulative population doubling levels (CPDL) compared to adult LPP-ECFCs (during the same time of culture ex vivo). In contrast to other populations of endothelial progenitor cells isolated from cord blood utilizing different methodologies, cord blood HPP-ECFC progeny uniformly express endothelial cell antigens and not hematopoietic specific cell antigens. Thus, HPP-ECFC are enriched in human umbilical cord blood and were not found in adult peripheral blood. HPP-ECFC were also found in endothelial cells derived from mammalian blood vessels e.g. umbilical vein and human aortic vessels. (FIGS. 1A-1F) These HPP-ECFCs appear in cultures of freshly plated cord blood mononuclear cells within 10 days, whereas adult blood LPP-ECFCs rarely appear before 14 days after plating.

Further, cord blood colonies consistently appeared larger compared to adult colonies (FIGS. 1A-1F). There were distinct differences in the size, frequency and time of appearance between adult and cord blood endothelial cell colonies. (FIGS. 1A-1F, 3, and 10A-10D) These observations show that cord blood EPCs are composed of HPP-ECFC, LLP-ECFC, and clusters, whereas adult blood EPCs are composed of LPP-ECFCs and clusters.

The complete hierarchy of HPP-ECFC, LPP-ECFC, clusters and mature endothelial cells can be isolated from any blood vessel in a living mammalian donor.

Figure 7:
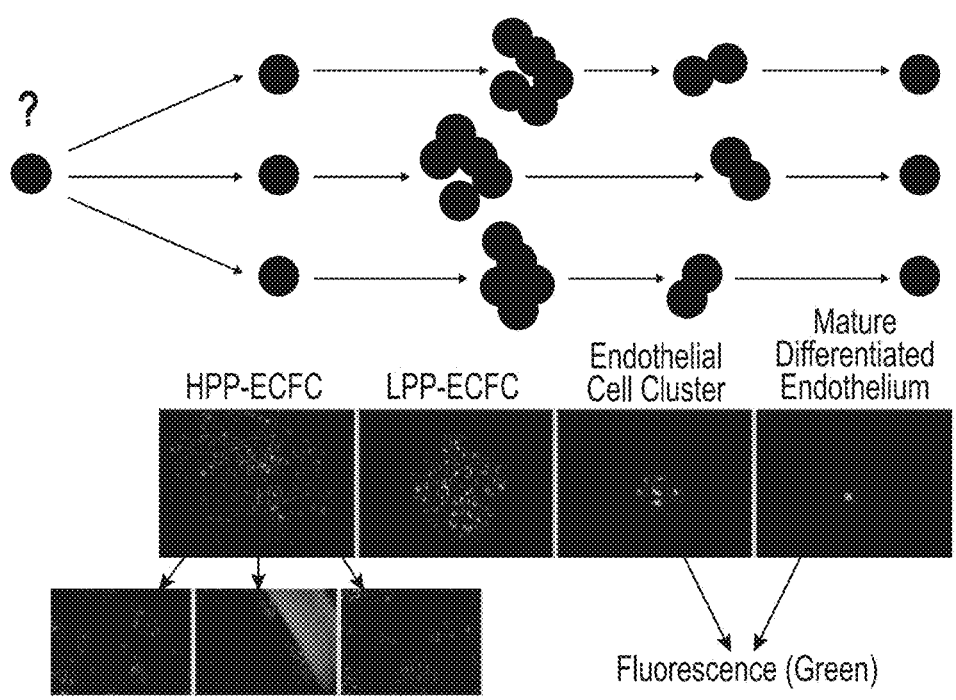
FIG. 7. Model of an endothelial progenitor cell hierarchy based on the proliferative and clonogenic potential of discrete populations of progenitor cells. High proliferative potential-endothelial colony forming cells (HPP-ECFC) are large colonies arising from single cells that form at least secondary colonies upon replating. HPP-ECFC give rise to all subsequent stages of endothelial progenitors in addition to replating into secondary HPP-ECFCs. Low proliferative potential-endothelial colony forming cells (LPP-ECFC) arising from single cells form colonies which contain greater than 50 cells, but do not form secondary colonies of LPP-ECFCs upon replating. Endothelial cell clusters (EC-clusters) can arise from a single cell but contain less than 50 cells, which are typically larger compared to the smaller cells (See FIGS. 10A-10D) found in HPP-ECFC and LPP-ECFC colonies. Mature terminally differentiated endothelial cells do not divide.
Figure 8A:
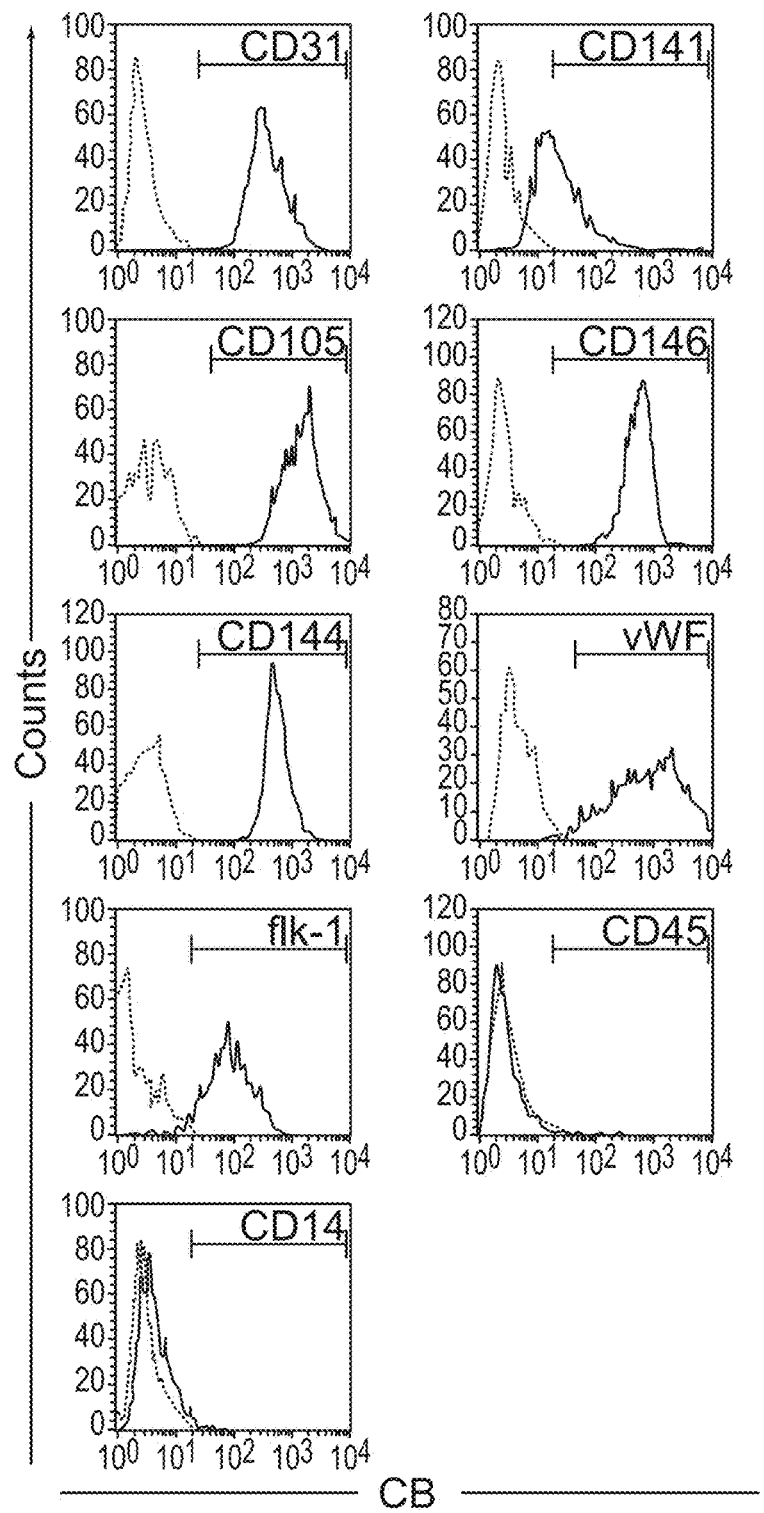
FIGS. 8A-8C. Immunophenotypic analysis of endothelial cells from cord blood-EPC, HUVECs, and HAECs.
Figure 8B:
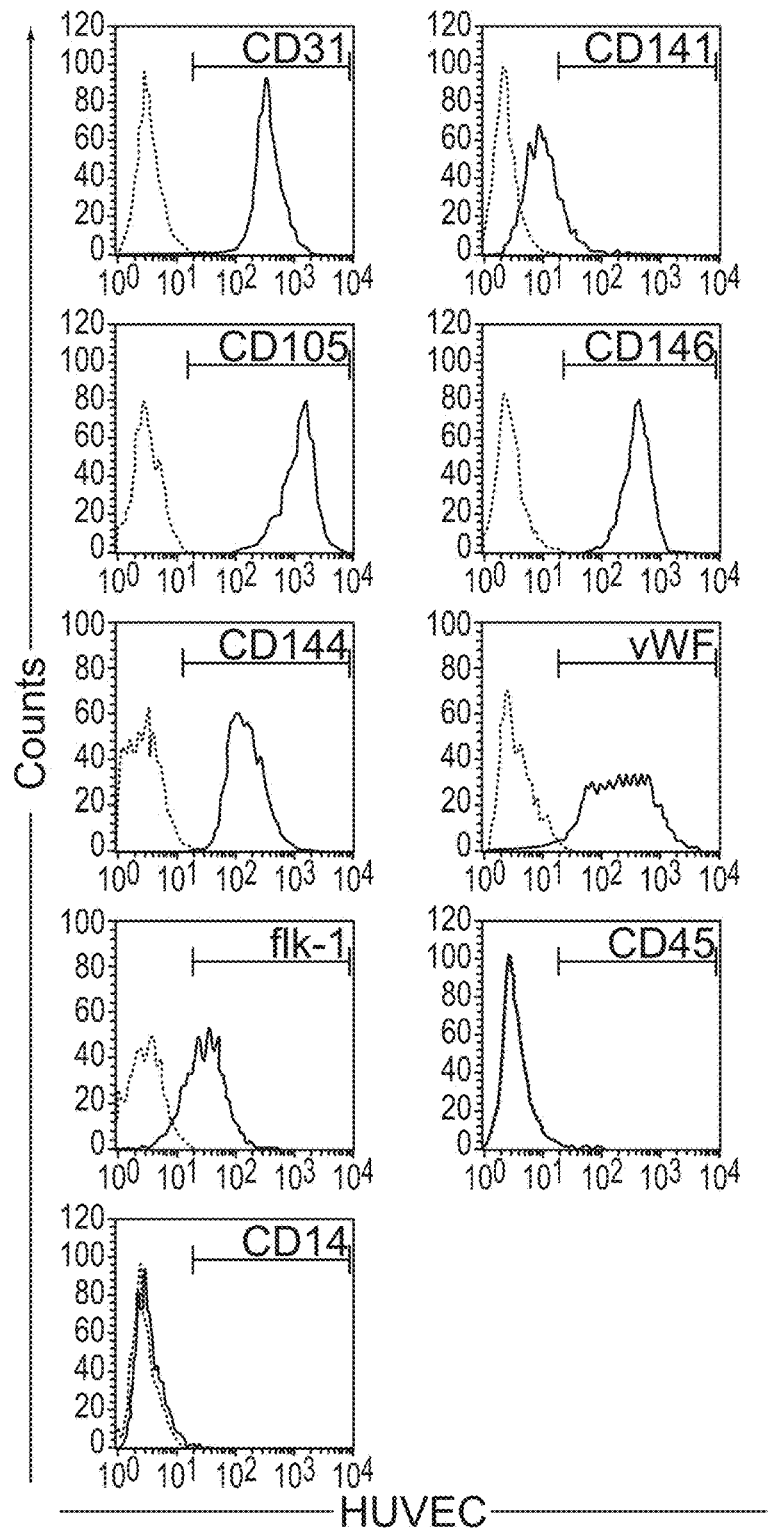
Figure 8C:
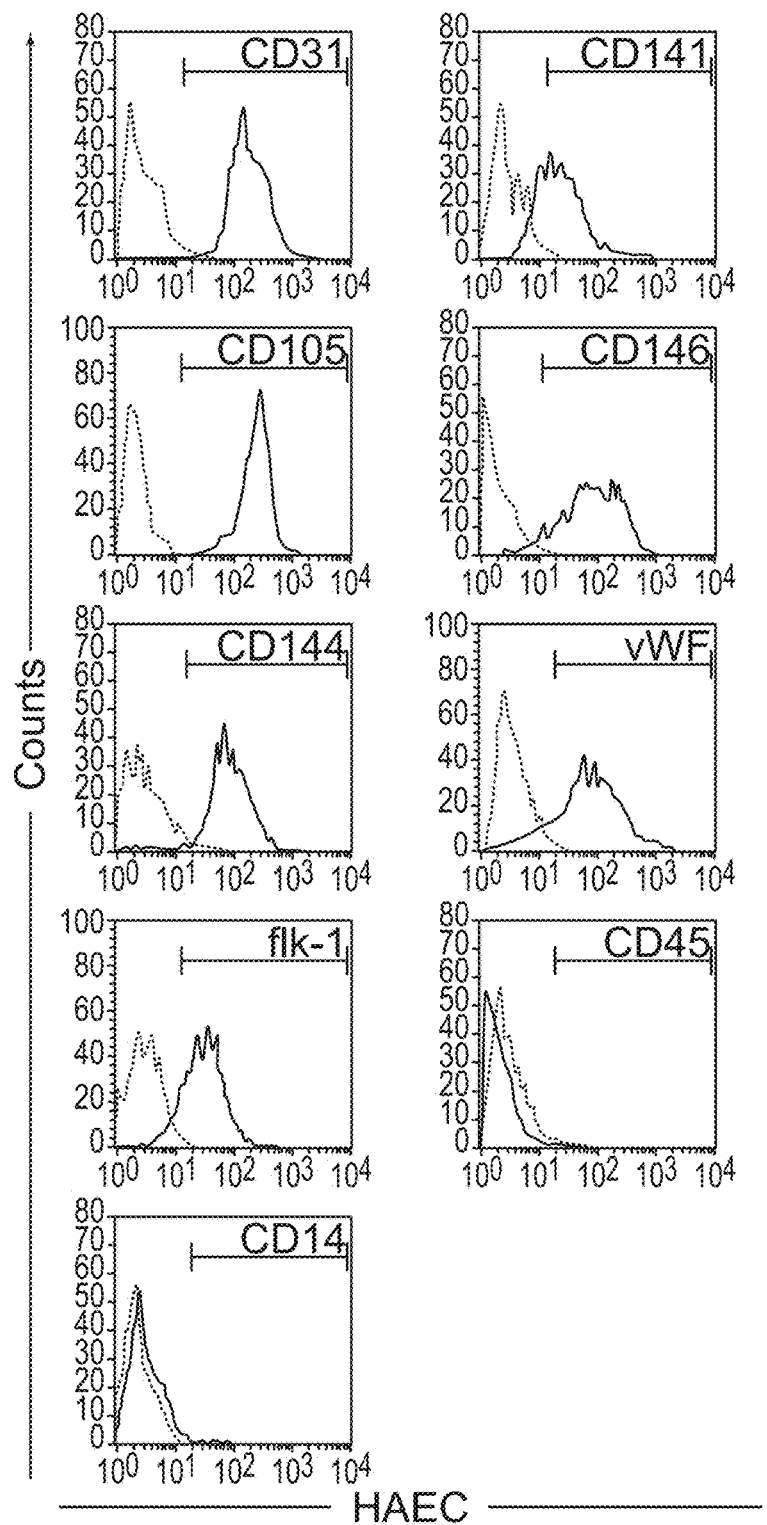
Figure 9A:
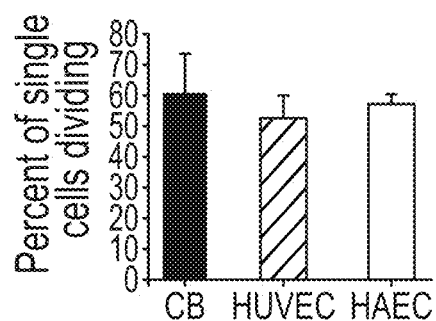
FIGS. 9A-9F. Quantitation of the clonogenic and proliferative potential of single endothelial cells derived from cord blood-EPC colonies, HUVECs, and HAECs.
Figure 9B:
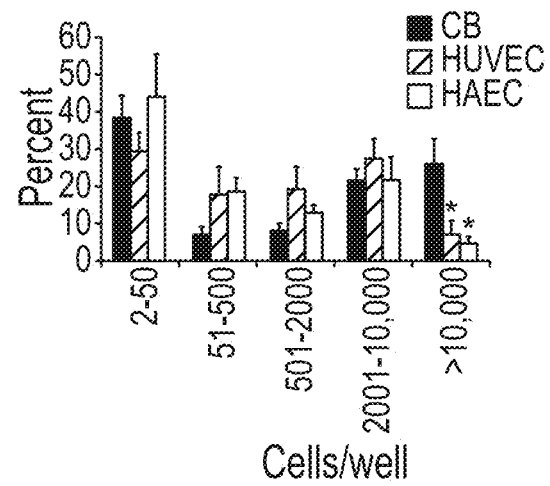
Figure 9C:
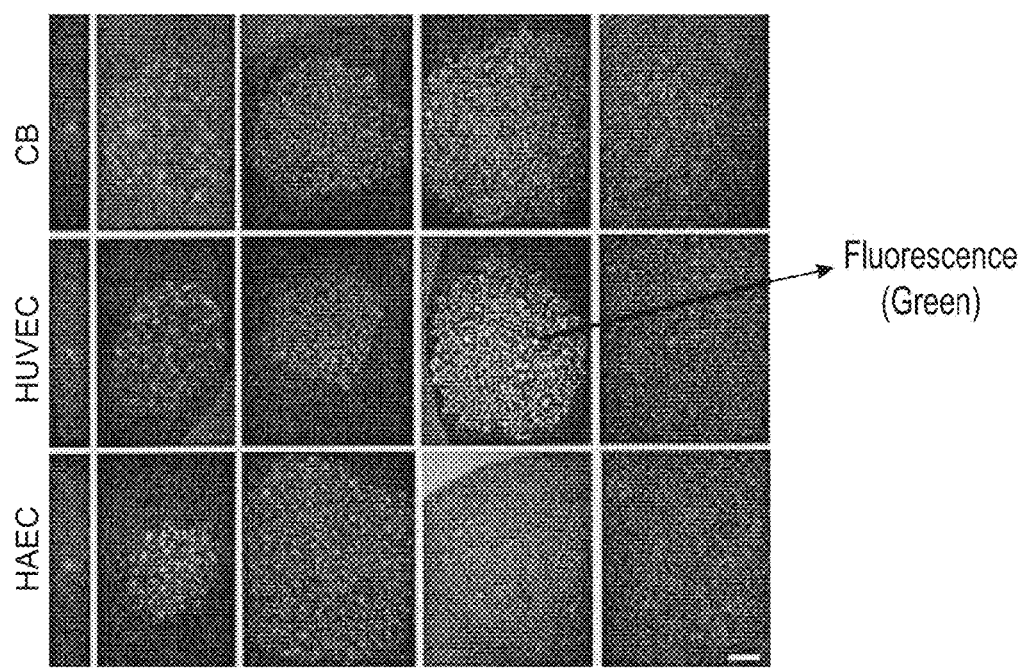
Figure 9D:
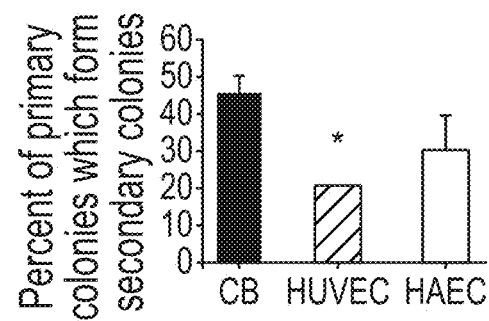
Figure 9E:
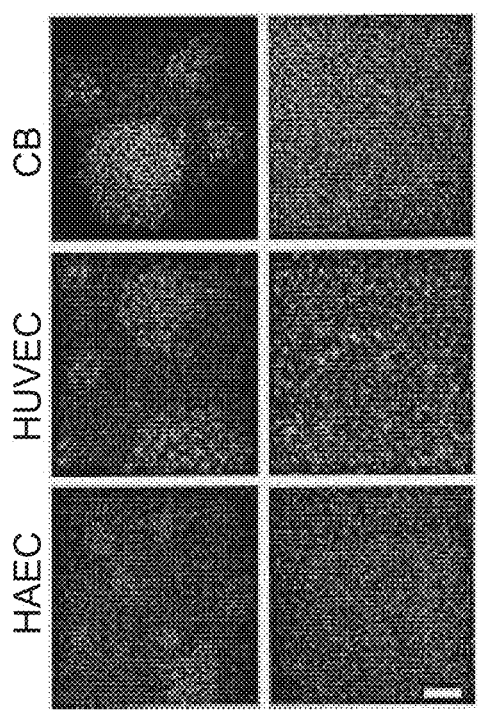
Figure 9F:
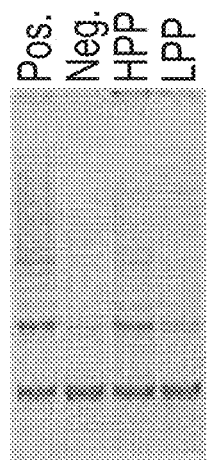
Figure 10A:
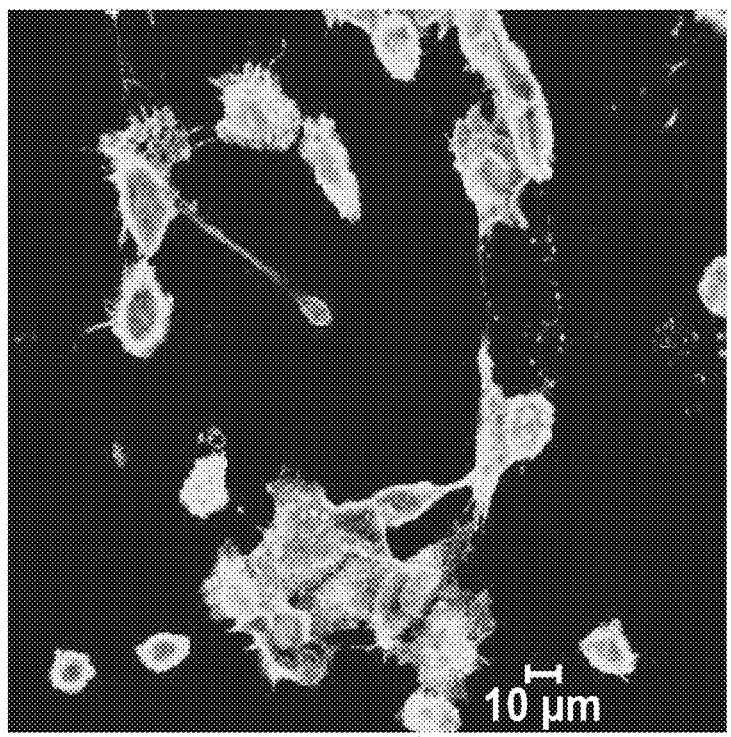
FIGS. 10A-10D. Monochromatic images of (FIG. 10A) HPP-ECFC, (FIG. 10B) LPP-ECFC, (FIG. 10C) endothelial clusters, and (FIG. 10D) mature differentiated endothelial cells. The HPP-ECFC are small cells (nuclear diameter 8-10 microns) with minimal cytoplasmic spreading (diameters vary from 12-22 microns) with nuclear to cytoplasmic ratio >0.8. LPP-ECFC are more heterogenous in size but are larger than HPP-ECFC. LPP-ECFC nuclei vary in size from 10.5-12.5 microns and have more cytoplasmic spreading (varying from 25-60 microns) with a ratio >0.4 but <0.5. Endothelial clusters are nearly mature endothelial cells with nuclei that vary from 13.0-16.5 microns and have cytoplasmic diameters that vary from 65-80 microns and nuclear to cytoplasmic ratios of >0.2 but <0.3. Mature differentiated endothelial cells are large very well spread cells with nuclear diameters that range from 17.0-22.0 microns and cytoplasmic diameters from 85-105 microns and nuclear to cytoplasmic ratios similar to endothelial clusters. Therefore, HPP-ECFC are very distinctly smaller than any of the other EPC and quite smaller than the mature endothelial cells.
Figure 10B:
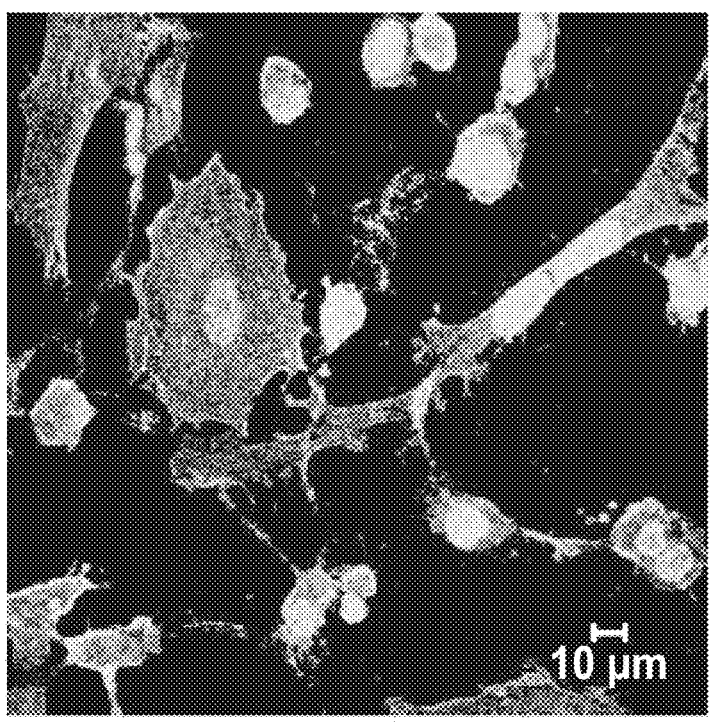
Figure 10C:
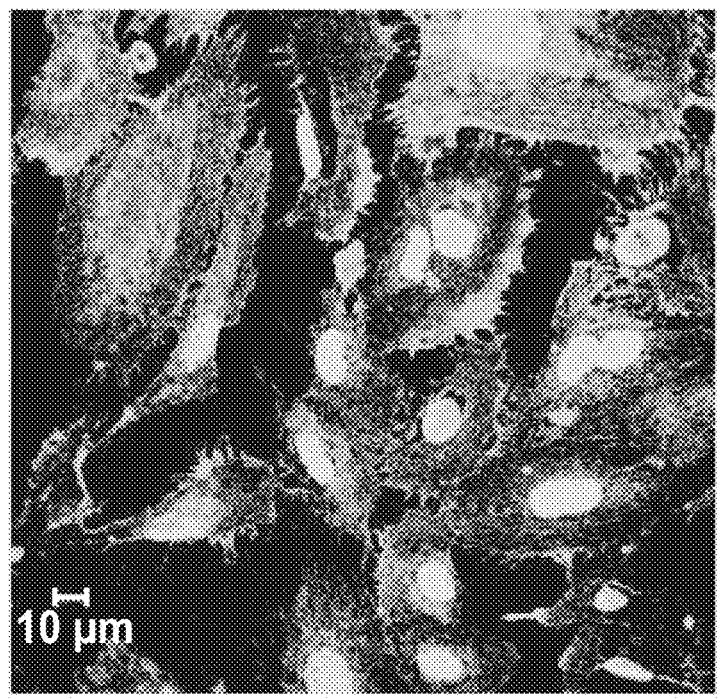
Figure 10D:
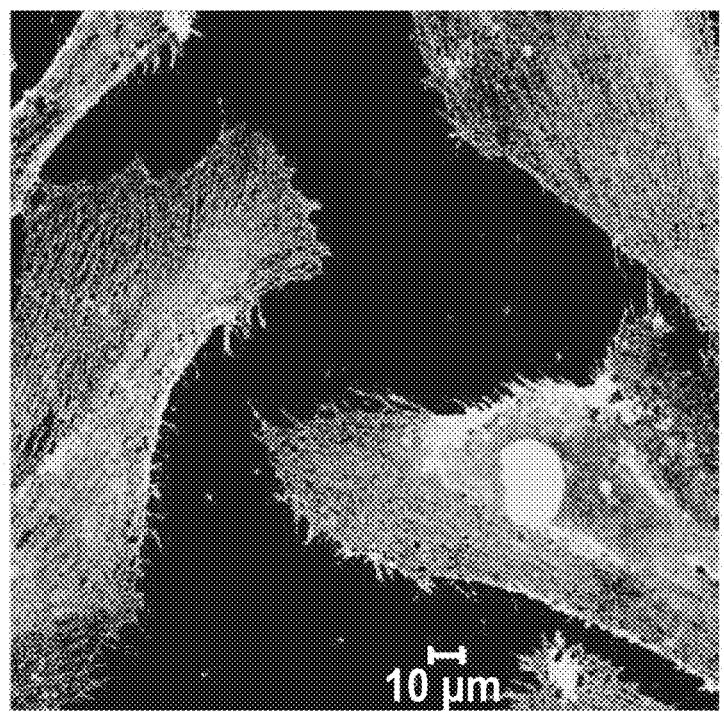
Figure 11:
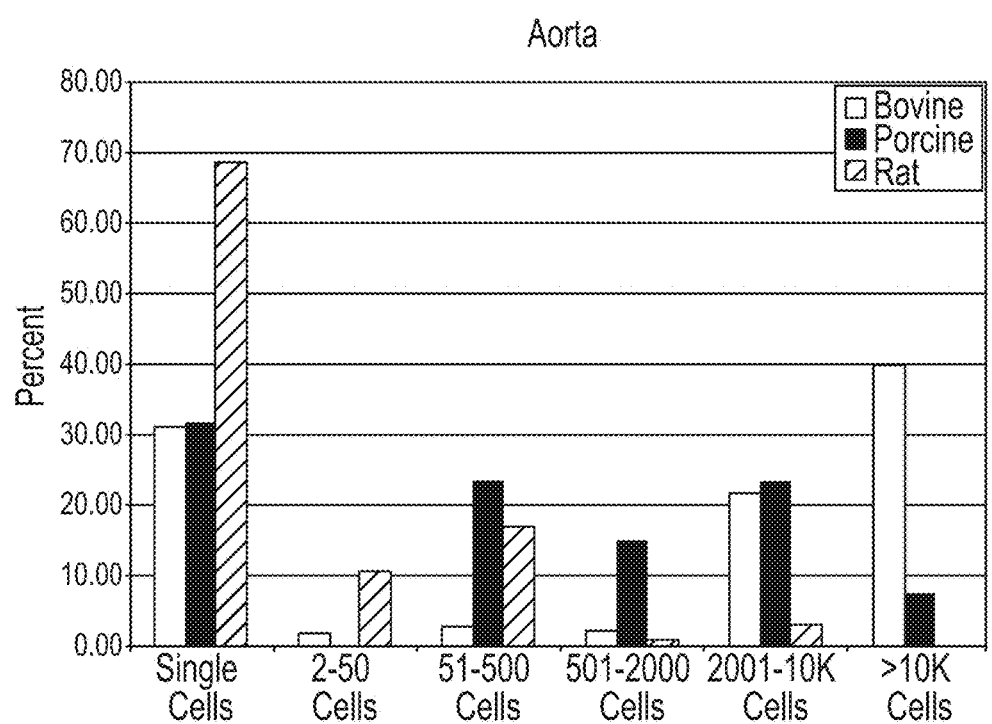
FIG. 11. The percent of dividing single plated bovine, porcine, and rat aortic endothelial cells giving rise to colonies of distinct classified sizes.

EPCs can be identified using similar terminology to that utilized for defining hematopoietic cell progenitors (FIG. 7). HPP-ECFCs give rise to all subsequent stages of endothelial progenitors in addition to replating into secondary HPP-ECFCs. Low proliferative potential-endothelial colony forming cells (LPP-ECFC) arising from single cells form colonies, which contain greater than 50 cells, but do not form at least secondary LPP-ECFC colonies upon replating. They do give rise to endothelial cell clusters (less than 50 cells). Finally, endothelial cell clusters can arise from a single cell but contain less than 50 cells, and do not replate into colonies or clusters.

Hematopoietic stem and progenitor cells are enriched in umbilical cord compared to adult peripheral blood. One intriguing observation was that EPCs were also enriched in umbilical cord blood compared to adult peripheral blood. Further, cord blood derived EPCs contain high levels of telomerase activity, which may account for the observation that these cells can be expanded for at least 100 population doublings without obvious signs of cell senescence. At the single cell level, some cord blood EPC-derived cells can be expanded $10^7$ to $10^{12}$ fold. To our knowledge, no other primary mammalian endothelial progenitor or mature cell has been identified with similar growth characteristics or clonogenic capacity.

Characterization of Endothelial Cell Colonies (EPCs) Isolated from Human Umbilical Cord Blood Cells were expanded in culture while maintaining an endothelial cell phenotype. In contrast to previously described endothelial progenitor cells isolated from cord blood, the present invention relates that cells isolated from human umbilical cord blood, i.e. cord blood HPP-ECFCs and progeny, can be cultured for at least 100 population doublings and expanded exponentially even when beginning with a single cell. Further, these cells do not express the hematopoietic cell specific surface antigens, CD45 and most also do not express CD14, and do not form hematopoietic cell colonies in methycellulose assays. In addition, the HPP-ECFC progeny rapidly form vessels in MATRIGEL® (extracellular matrix proteins), upregulate VCAM-1 in response to either IL-1 or TNFα stimulation, and express endothelial cell specific antigens, which confirms their endothelial cell identity. These cells were designated high proliferative potential-endothelial colony forming cells (HPP-ECFCs).

Cord blood HPP-ECFCs demonstrate greater replicative kinetics compared to adult blood (which are composed of LPP-ECFC, clusters, and mature endothelial cells). While endothelial progenitors are reported to express AC133, CD34, and Flk1, HPP-ECFC progeny and EOC progeny display similar frequencies of cells expressing AC133, CD34, and Flk1 antigens and, therefore, these cell surface markers do not permit discrimination of cells with differing proliferative potentials.

Endothelial outgrowth cells appear two to four weeks after culture of MNCs isolated from adult peripheral blood and are characterized by their exponential growth in vitro (however, EOC display lower levels of telomerase, do not replete into secondary LPP-ECFC, and reach replicative senescence long before TPP-ECFC). In contrast, HPP-ECFC generated from human umbilical cord blood MNCs, emerged five to ten days after culture of cord blood MNCs in complete EGM-2 media on tissue culture plates coated with type I collagen. Discrete adherent cell colonies appeared and displayed the "cobblestone" morphology of endothelial cells (FIGS. 1C-1F). The morphology and appearance of the colonies was similar to, but distinct from, that previously described for adult peripheral blood derived EOC colonies and clearly distinct from adherent circulating endothelial cells or macrophages. The HPP-ECFC colonies are large and are composed of a mixture of small round, long thin, and large flattened round cells whereas the EOC are nearly homogenously composed of long thin cells. The colony-derived cells were subcultured and expanded cells derived from these colonies were used for immunophenotyping, functional testing and measurement of growth kinetics. After initial passage, the cells formed monolayers of spindle shaped cells with "cobblestone" morphology. Immunophenotyping revealed that the cells uniformly expressed the endothelial cell surface antigens, CD31, CD141, CD105, CD146, CD144, vWF, and flk-1 (FIGS. 2A-2B). The cells did not express the hematopoietic cell surface specific antigens, CD45 and CD14, confirming that the monolayers were not contaminated with hematopoietic cells. (FIGS. 1A-1F, 3, and 10A-10D).

Figure 2A:
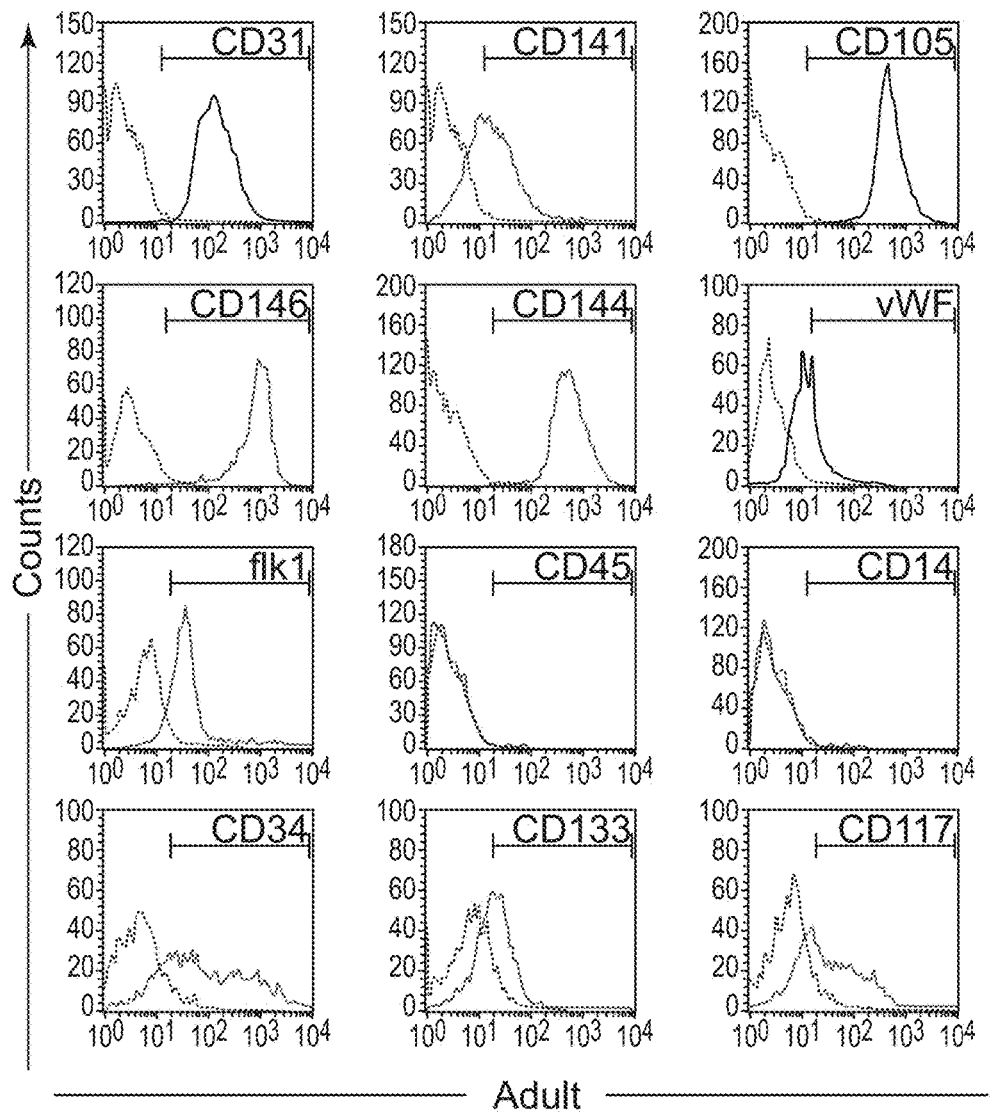
FIGS. 2A-2E. Phenotypic and functional analysis of adult and cord blood EPC-derived endothelial cells.
Figure 2B:
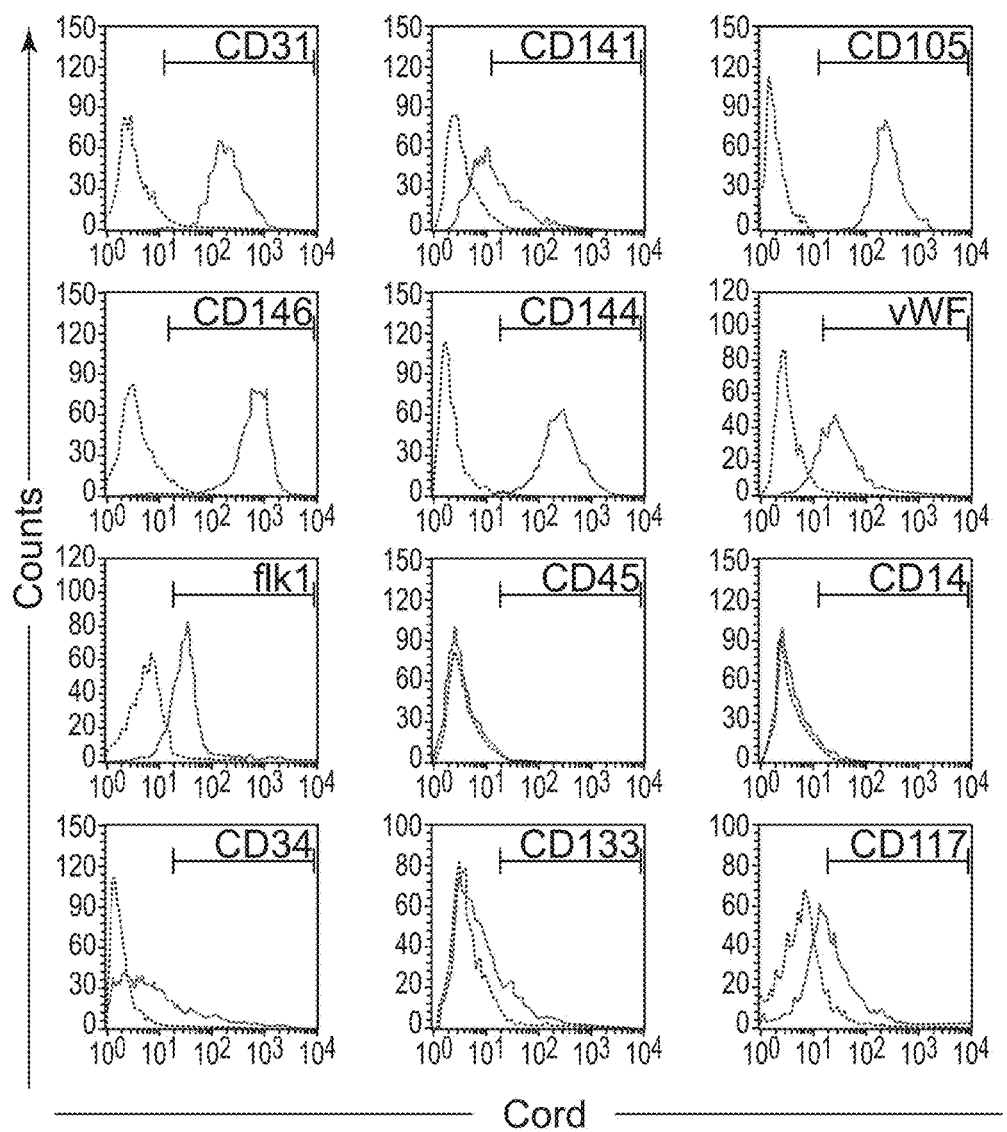
Figure 2C:
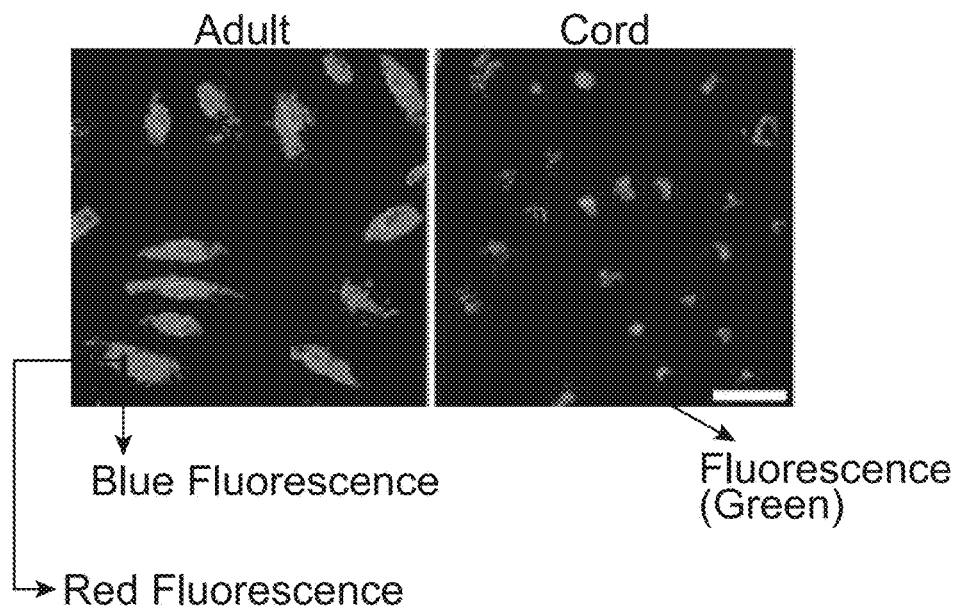
Figure 2D:
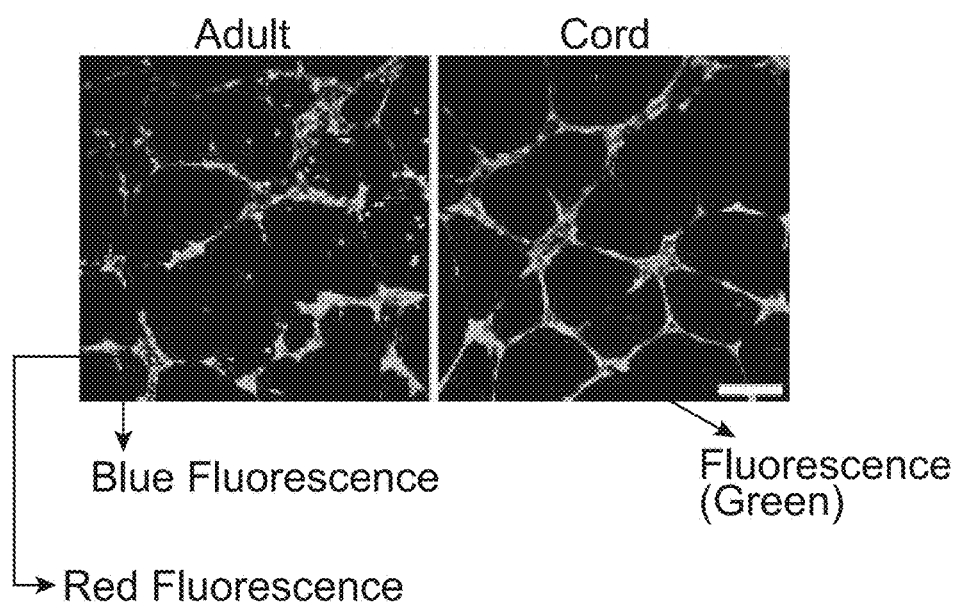
Figure 2E:
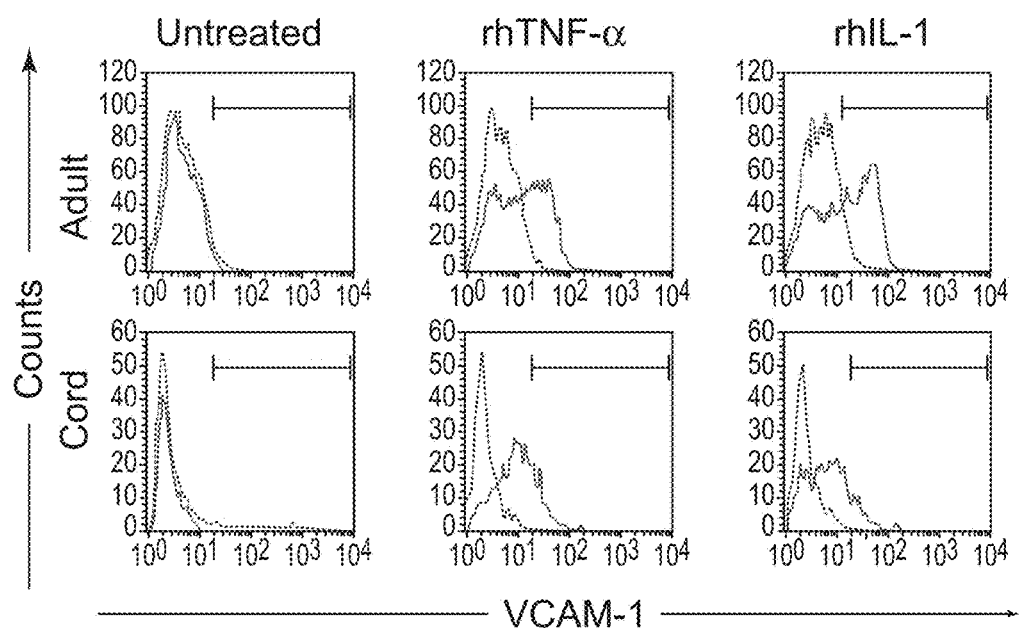

Confirming that the monolayers derived from the adherent colonies were endothelial cells, the cells ingested acetylated-low density lipoprotein (Ac-LDL) or (Dil-AC-LDL). These cellular functions are characteristic of endothelial cells. Cells subcultured from the adherent colonies uniformly incorporated Ac-LDL, formed vessels in MATRIGEL® (extracellular matrix proteins) after seeding varying numbers of cells, and upregulated VCAM-1 in response to both rhTNF-α or rhIL-1 stimulation (FIGS. 2C-2E).

The growth kinetics of cord blood HPP-ECFC and progeny were measured as a function of time. Strikingly, cord blood HPP-ECFC and progeny could be exponentially expanded in culture for at least 100 population doublings without signs of senescence, and the number of cells increased $10^{20}$ fold over a period of 100 days in culture. A representative growth curve of cord blood endothelial cells, illustrates the proliferative potential of these cells in vitro. Thus, based on immunophenotyping, functional testing, and an analysis of growth kinetics, it was shown that colonies of endothelial cells (designated HPP-ECFCs) can be uniquely cultured from cord blood MNCs and passaged into confluent monolayers of exponentially expandable endothelial cells.

HPP-ECFC Colonies are Present in Human Umbilical Cord Blood but not in Adult Peripheral Blood 50-100 milliliters of peripheral blood was collected from healthy adult donors or from umbilical cords of normal term infants and isolated MNCs. Cells were seeded into tissue culture plates coated with extracellular matrix molecules in complete EGM-2 media and observed for colony formation over the next one to six weeks. The number of colonies per equivalent volume of blood was increased 15 fold in cord blood compared to adult peripheral blood (Table I, FIGS. 1A and 1B). Similar differences in colony formation were also observed when equivalent numbers of cord and adult MNCs were plated. Although adult EOC colonies typically formed between 2-4 weeks after initiation of culture, cord blood HPP-ECFC colonies appeared within 5-10 days. Finally, immunophenotyping of the cells isolated from endothelial colonies from both cord blood and adult peripheral blood by flow cytometry revealed that the colony-cells uniformly expressed the endothelial cell surface antigens, CD31, CD105, CD146, CD144, vWF, and flk-1 and not the hematopoietic cell surface antigens CD45 and CD 14, confirming their endothelial cell identity. Immunophenotyping of the adult EOCs was consistent with previously published studies. Thus, endothelial colony forming cell HPP-ECFC are present in cord blood and represent a different cell type compared to adult peripheral blood EOCs (which represent LPP-ECFCs).

The Proliferative Rate of Cord Blood HPP-ECFCs is Greater than Adult Blood EOCs

Given the differences in the frequency and the time of appearance of colony formation of cells from cord blood compared to adult peripheral blood, a question was whether there were differences in the proliferative kinetics of adult and cord blood cells. Early passage monolayers of HPP-ECFC were established from cord blood and EOC established from adult peripheral blood, and cells were cultured in complete EGM-2 media on type I collagen coated plates. Input cell numbers were counted for determination of population doubling times (PDT) and cumulative population doubling levels (CPDL) in long-term cultures, which were measurements used to quantitate and to compare the proliferative kinetics of cord blood and adult blood derived cells. Cells were cultured for at least 10 passages to accurately quantitate the PDT and CPDL. Results testing multiple cell lines from different donors, showed that there was a 2.5 fold decrease in the PDT of cord blood HPP-ECFCs compared to adult EOC controls. Further, consistent with a decrease in PDT, culture of cord blood cells demonstrated a significant increase in CPDLs compared to serial passage of adult EOCs. Thus, although both cord and adult cells can be expanded in culture, the proliferative potential of cord blood HPP-ECFC and progeny is greater compared to adult EOC. Cord blood derived HPP-ECFC also demonstrate greater proliferative potential at the single cell level compared to adult blood EOCs.

The proliferative and clonogenic capacity of individual cord blood HPP-ECFC-derived endothelial cells or adult EOCs at the single cell level was determined. A novel experimental method was designed to quantitate the proliferative and clonogenic capacity of single cord blood HPP-ECFC-derived endothelial cells and adult EOCs.

Early passage cord blood HPP-ECFC-derived endothelial cells or adult EOC progeny were initially transduced with a retrovirus encoding a green fluorescent protein (GFP) and selected for expression of GFP. Transduction efficiency of both cord and adult endothelial cells was greater than 95%. Following selection, one GFP expressing HPP-ECFC-derived endothelial cell or adult EOC-derived endothelial cell was plated by fluorescent cytometry sorting (using a sorting nozzle with a diameter ≥100 microns and a sheath flow pressure of ≤9 pounds per square inch) into one well of a 96 well tissue culture plate coated with type I collagen and filled with 200 µl of EGM-2 media. Immediately following placement, individual wells were examined to ensure that only one endothelial cell had been placed into each well. Endothelial cells were then cultured for 14 days, and one half of the media was changed every 4 days with fresh EGM-2 media. At the end of 14 days, the number of GFP expressing endothelial cells was counted.

The number of single cells undergoing at least one cell division was significantly greater for cord blood HPP-ECFC-derived endothelial cells compared to adult EOC-derived endothelial cells. In scoring the number of cells in each well at the end of 14 days, it was clear that single cord blood HPP-ECFC-derived endothelial cells divided more and produced larger colonies compared to adult EOC-derived endothelial cells. Because of differences in the capacity of single cord blood HPP-ECFC-derived endothelial cells to divide and form colonies compared to adult EOC-derived endothelial cells, the number of cells in each well, which demonstrated at least one cell division, were counted. Although, most of the single adult EOC-derived endothelial cells (which had divided), produced clusters of between 2 and 50 cells, some did give rise to secondary colonies of up to 500 cells, but only a single colony of >2000 cells arose from any of the single sorted adult EOC-derived endothelial cells. However, greater than 60% of the cord blood HPP-ECFC-derived endothelial cells (which had divided), formed well circumscribed secondary colonies consisting of at least 2000 cells, and numerous single sorted cells gave rise to colonies composed of >10,000 cells (to the inventors' knowledge, no adult EOC-derived endothelial cells ever produced such a colony).

Secondary cell colonies derived from either single adult EOC-derived or cord blood HPP-ECFC-derived endothelial cells were serially replated to determine if these cells could form more colonies. Secondary colonies derived from single adult EOC-derived endothelial cells never gave rise to tertiary colonies after replating in 24 well or 6 well type I collagen coated tissue culture plates in multiple independent experiments. Single cells plated remained quiescent and did not proliferate. However, most of the secondary colonies derived from single cord blood HPP-ECFC-derived endothelial cells, which produced greater than 2000 cells, could be replated under the same experimental conditions to form tertiary endothelial colonies. Single primary cord blood HPP-ECFC-derived endothelial cells can produce secondary colonies, which can be subsequently serially passaged to produce from $10^7$-$10^{12}$ endothelial cells.

Given the similarities of this unique and newly identified population of cord blood derived endothelial colony forming cells to the hematopoietic high proliferative potential-colony forming cells (HPP-CFC; the most primitive multipotent hematopoietic progenitor that can be cultured in an in vitro clonogenic assay) these cells are named "high proliferative potential-endothelial colony forming cells (HPP-ECFC)". In summary, these cells are different from the previously described adult EOCs in the following ways: (1) HPP-ECFCs have higher proliferative kinetics when cultured under the same experimental conditions as adult EOCs, (2) HPP-ECFCs appear at earlier timepoints in culture from plated cord blood MNCs compared to adult EOCs derived from plated adult peripheral MNCs, (3), HPP-ECFCs have higher clonogenic potential at the single cell level compared to adult EOCs. (4) HPP-ECFCs can be serially replated to form at least secondary HPP-ECFC colonies while/whereas adult EOCs do not display this potential, and HPP-ECFC display high levels of telomerase.

Growth Kinetics of EPC-Derived Cord Blood and Adult Endothelial Cells

Figure 3:
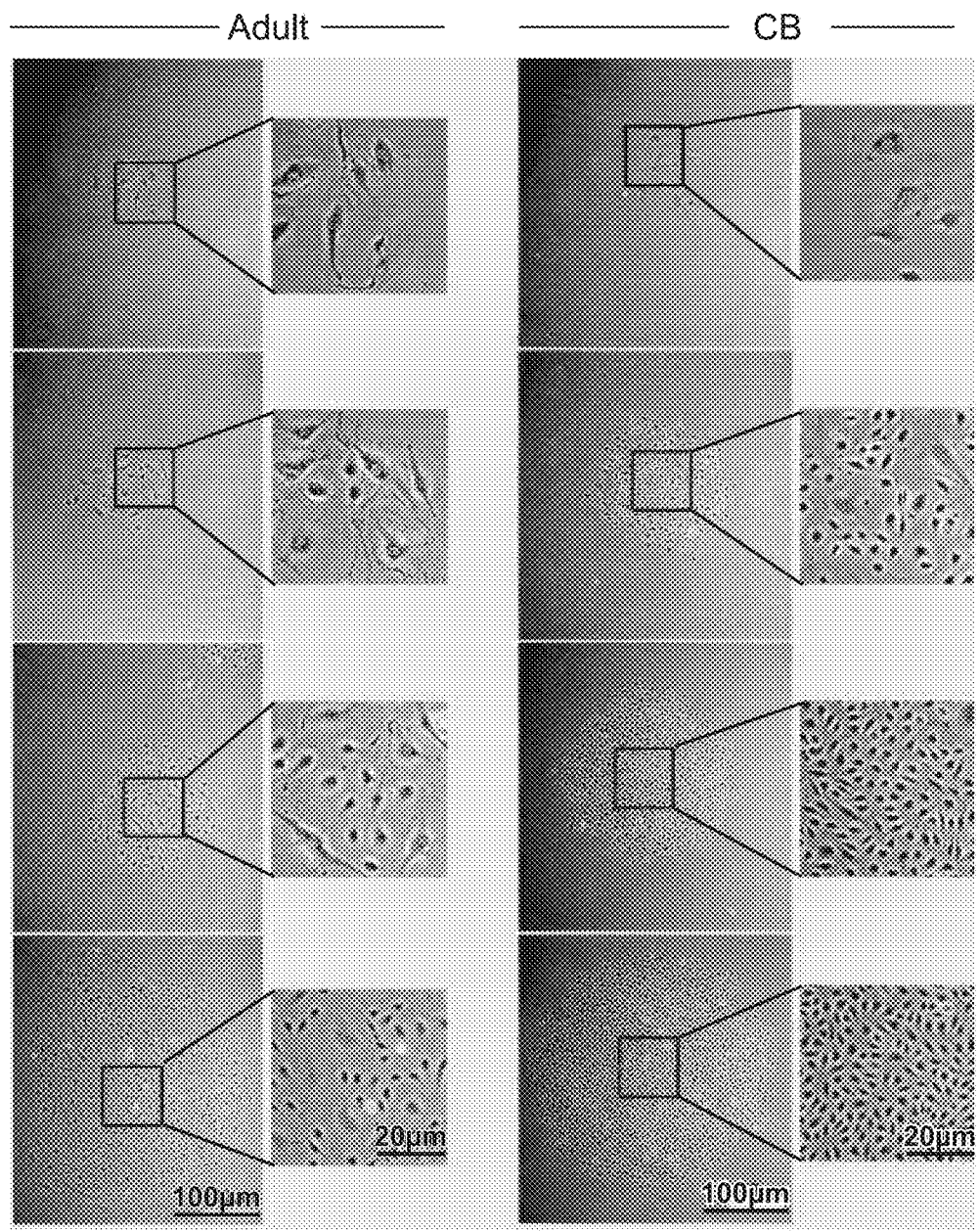
FIG. 3. Representative photomicrographs of morphologically distinctly different secondary colonies, which formed seven days after adult and cord blood (CB) EPC-derived endothelial cells were re-plated at low cell density.

Progenitor cells of different lineages are defined and discriminated by their clonogenic and proliferative potential. Because of the differences in cord blood and adult EPC colony formation, the proliferative kinetics of EPC-derived cord blood and adult endothelial cells were compared. Initially cells derived from cord blood and adult endothelial cell colonies were plated at limiting cell dilutions to test whether the cells would form secondary colonies and grow to confluence. Interestingly, the cell progeny derived from both adult and cord blood EPC colonies formed secondary cell colonies of various sizes before growing to confluence (FIG. 3). However, colonies derived from cord blood EPC-derived cell progeny were consistently larger and contained smaller cells compared to adult colonies (FIG. 3).

Figure 4A:
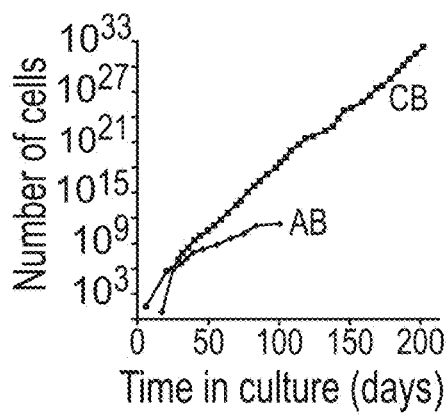
FIGS. 4A-4D. Growth kinetics of the endothelial cell progeny derived from cord and adult endothelial progenitor cell colonies.
Figure 4B:
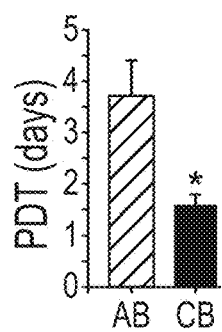
Figure 4C:
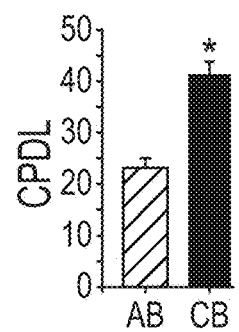

Cell monolayers were serially passaged to determine the proliferative potential of EPC-derived cord blood and adult endothelial cells. Remarkably, cord blood EPC-derived cells could be expanded for at least 100 population doublings without obvious signs of senescence. In contrast, adult EPC-derived cells could be passaged for only 20-30 population doublings (FIG. 4A). To quantitate and compare the proliferative kinetics of cord blood and adult EPC-derived cells, the population doubling times (PDT) and cumulative population doubling levels (CPDL) were calculated during a defined time in culture (60 days). There was a 2.5 fold decrease in the PDT and a 1.5 fold increase in the CPDLs of cord blood EPC-derived cells compared to adult EPC-derived cells (FIGS. 4B and 4C). The PDT and CPDL of adult EPCs was similar to two recent reports, which tested the proliferative kinetics of EPC-derived cells isolated from healthy adult donors.

Figure 4D:
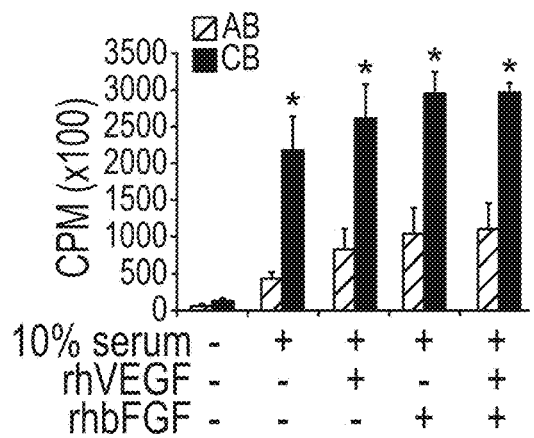

The proliferation of cord blood and adult EPC-derived cells in response to either rhVEGF or rhbFGF stimulation, which are two endothelial cell mitogens were compared. Cord blood and adult EPC-derived cells were serum starved and then cultured in the presence or absence of either rhVEGF or rhbFGF. Cells were cultured for 16 hours, and pulsed with tritiated thymidine before harvest to measure DNA synthesis. Cord blood EPC-derived cells displayed greater DNA synthesis in response to either rhVEGF or rhbFGF stimulation compared to adult EPC-derived cells (FIG. 4D). Collectively, these results demonstrate that the proliferative rate and expandability of cord blood EPC-derived cells is greater than adult EPC-derived cells in both short and long term assays. Further, cord blood and adult EPC-derived endothelial cells form distinct cell colonies of various sizes and morphology when plated at limiting dilution.

Quantitation of the Clonogenic and Proliferative Potential of Single Cord Blood and Adult Endothelial Cells Derived from EPC Colonies Cord blood and adult EPC colonies yield cells with different proliferative and clonogenic potential. However, a rigorous test for the clonogenic potential of a progenitor cell is to determine whether a single cell will divide and form a colony in the absence of other cells. Therefore, an assay was developed to quantitate the proliferative and clonogenic potential of single cord blood and adult endothelial cells derived from EPC colonies.

Cord blood and adult endothelial cells derived from the initial EPC colonies were transduced with a retrovirus encoding EGFP and selected for EGFP expression. Following selection, one EGFP expressing endothelial cell was plated by FACS into one well of a 96 well tissue culture plate coated with type I collagen and filled with complete EGM-2 media. Endothelial cells were cultured, and the number of EGFP-expressing endothelial cells was counted at the end of 14 days as disclosed herein. This method is illustrated in FIG. 5A.

Figure 5B:
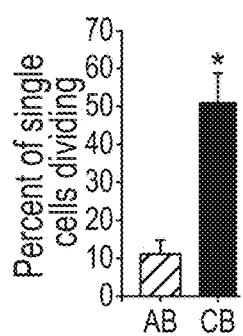
Figure 5C:
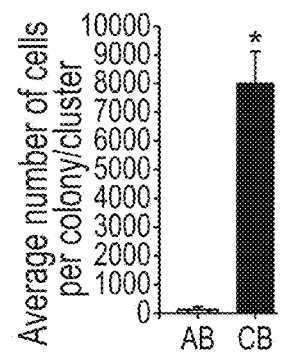
Figure 5D:
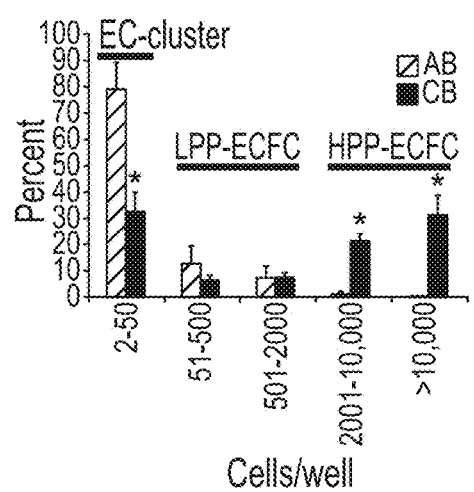
Figure 5E:
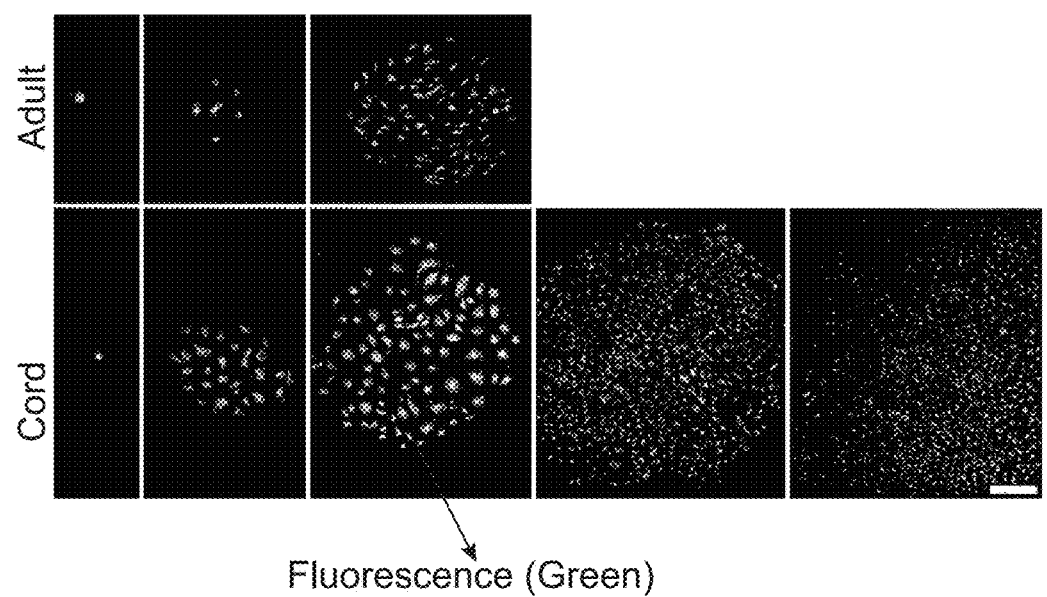

Remarkably, the percentage of single cells undergoing at least one cell division was increased five fold for cord blood endothelial cells compared to adult cells (FIG. 5B). Further, the average number of cell progeny derived from a single cord blood endothelial cell was 100 fold greater compared to the number of cells derived from an individual adult cell (FIG. 5C). Greater than 80% of the single adult endothelial cells which divided gave rise to small colonies or clusters of cells ranging in number from 2-50 cells (FIG. 5D). However, some single adult endothelial cells did form colonies containing greater than 500 cells (FIG. 5D). In contrast, at least 60% of the single plated cord blood endothelial cells which divided formed well-circumscribed colonies containing between 2,000 and 10,000 cells in the 14 day culture period (FIG. 5D). Photomicrographs of the size and morphology of the various endothelial cell colonies and clusters of cells derived from a single cord blood or adult cell are shown in FIG. 5E. These single cell studies demonstrate that there are different types of cord and adult EPCs, which can be discriminated by their proliferative and clonogenic potential, and that EPCs display a hierarchy of proliferative potentials similar to the hematopoietic progenitor cell hierarchy.

The Cell Progeny of Single Cord Blood Endothelial Cells can be Serially Replated and Expanded Exponentially in Long-Term Cultures.

Figure 6A:
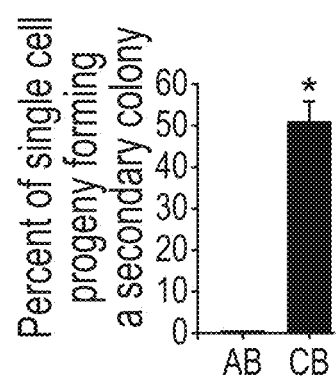
FIGS. 6A-6E. Replating potential and long-term culture of the cell progeny derived from a single cord blood or adult EPC-derived endothelial cell.
Figure 6B:
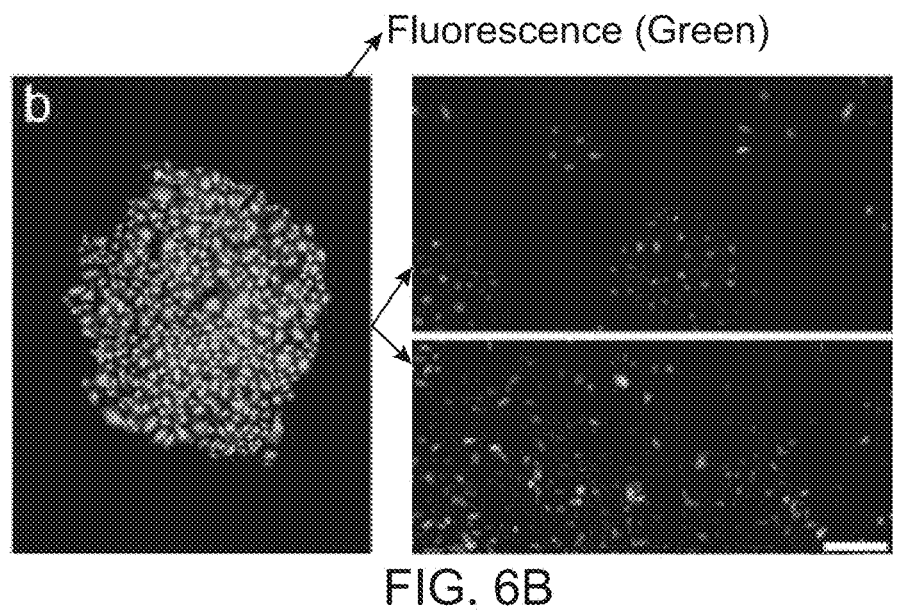

In the hematopoietic cell system, the most proliferative progenitor cell type is termed the high proliferative potential-colony forming cell (HPP-ECFC). The HPP-ECFC is defined by its ability to form large cell colonies, which yield individual cells that have the potential to form at least secondary colonies upon serial replating. The clonal progeny derived from a single plated cord blood or adult EPC-derived cell were trypsinized, replated and cultured into 24-well tissue culture plates for 7 days. After plating the clonal progeny of over 1000 single adult EPC-derived cells into 24 well plates, only one secondary colony was detected in the wells after 14 days of culture (FIG. 6A). In contrast, approximately one half (205 of 421) of the clonal progeny of single plated cord blood EPC-derived cells formed secondary colonies or rapidly grew to confluence in 24 well plates (FIG. 6A). A representative photomicrograph of the secondary endothelial cell colonies or confluent cell monolayers derived from the progeny of a single cord blood endothelial cell is shown in FIG. 6B. Since secondary colonies were not detected in those wells that had rapidly grown to confluence in 5 days, a limiting dilution analysis was performed on the confluent monolayer. At least nine percent of the single cells plated from this monolayer formed an endothelial cell colony, containing greater than 100 cells. This result verifies that individual cells derived from cord blood EPCs are capable of forming secondary colonies.

Figure 6C:
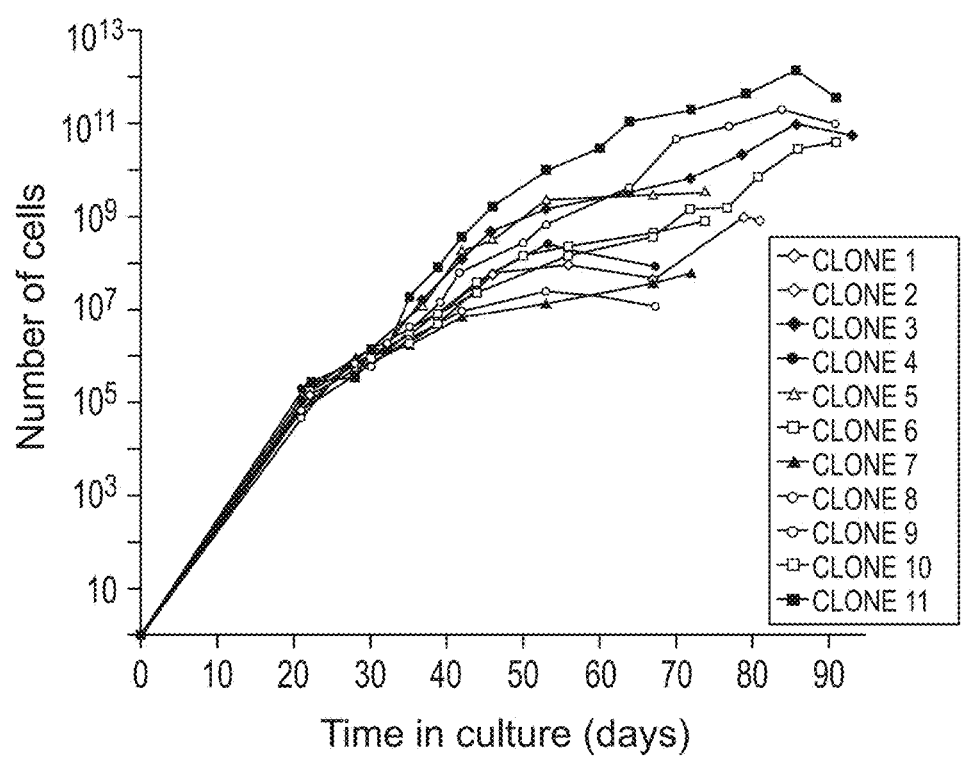

The long-term proliferative potential of the cells derived from a single plated cord blood EPC-derived endothelial cell was tested. Secondary colonies or confluent cell monolayers derived from single cord blood endothelial cells were serially passaged into progressively larger tissue culture plates. The cell progeny of 11 single endothelial cells, originally derived from three different cord blood donors were tested. Single cord blood endothelial cells yielded at least $10^7$ cells in long-term culture. (FIG. 6C). The average CPDL of the eleven single cord blood endothelial cells tested was 30.8. Thus, a population of high proliferative EPCs in cord blood, which form secondary and tertiary colonies.

EPC-Derived Cord Blood Endothelial Cells Contain High Levels of Telomerase Activity.

Figure 6D:
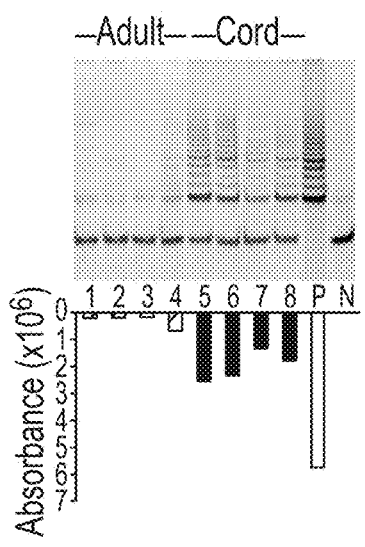
Figure 6E:
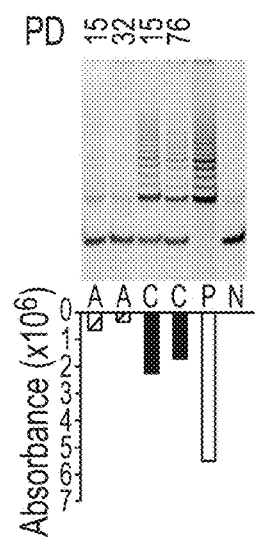

Endothelial cells derived from cord blood EPCs were serially passaged beyond Hayflick's limit for at least 100 population doublings (FIG. 4A). The only other reported primary endothelial cells with similar growth kinetics are those genetically engineered to overexpress telomerase. Thus, telomerase activity was measured in cord blood and adult EPC-derived cells as a potential molecular explanation for the differences in their growth kinetics. Both early and late passage cord blood EPC-derived progeny display significantly elevated levels of telomerase activity compared to adult EPC-derived cells, reminiscent of the previously described primary endothelial cells lines, which overexpress telomerase (FIGS. 6D-6E). Thus, consistent with extensive proliferative potential, cord blood EPC-derived cells retain high levels of telomerase activity (34±10% of the telomerase activity of an equal number of HeLa cells) with serial passage in culture.

Expansion of Repopulating Stem and Progenitor Cells Ex Vivo

Cord blood high proliferative potential-endothelial colony forming cell (HPP-ECFC) in co-culture with autologous or unrelated cord blood, mobilized adult peripheral blood, or marrow-derived HSC, expands the number of HSC cells and results in an increase in HSC and an increase HSC repopulating activity leading to higher levels of engraftment in a recipient subject.

Co-culture of HPP-ECFC from cord blood with human HSC increases hematopoietic progenitor cell numbers and enhances engraftment of human hematopoietic cells in NOD/SCID mice, an assay for in vivo measure of human HSC function.

Figure 12A:
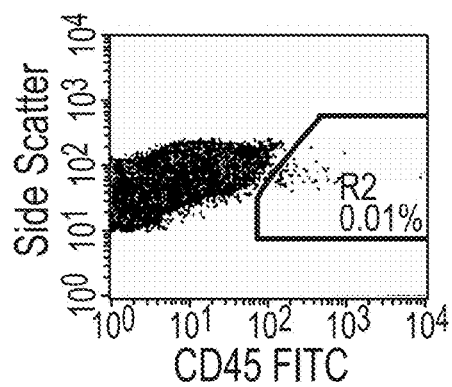
FIGS. 12A-12C. Percent chimerism of human cells (CD45 positive) detected by flow cytometry in the peripheral blood of NOD-SCID mice eight weeks after (FIG. 12A) transplantation of human bone marrow derived CD34+ cells injected on the same day of isolation.
Figure 12B:
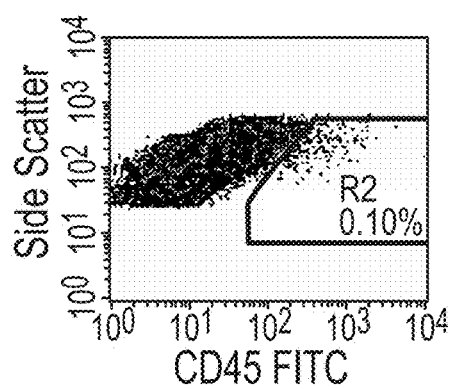
Figure 12C:
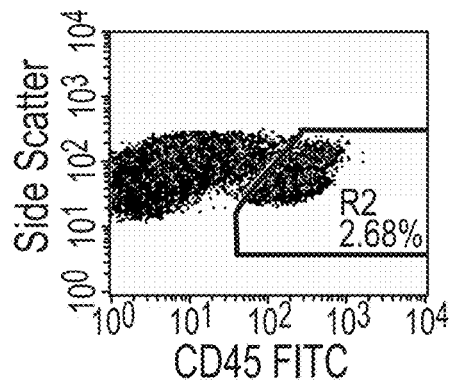

Human cord blood HPP-ECFC-derived endothelial cells co-cultured with human cord blood or mobilized adult peripheral blood $CD34^+CD38^-$ cells (enriched in HSC activity) for up to 7 days (with added cytokines) results in an enhancement in human $CD45^+$ cell engraftment in sublethally irradiated NOD/SCID mice by >100 fold (FIGS. 12A-12C).

A method of collection, isolation, and expansion of the HPP-ECFC and the particular method for co-culturing the HPP-ECFC with human stem cells are novel. HPP-ECFC can be collected from any cord blood sample, expanded, frozen, and stored. These cells can then be thawed, expanded, and used in co-culture to expand human cord blood, marrow-derived, or mobilized adult peripheral blood stem and progenitor cell samples. The expanded product can then be used for transplantation purposes (after regulatory agency approval).

Materials and Methods

Adult Peripheral and Umbilical Cord Blood Samples

Fresh blood samples (50-100 ml) were collected by venipuncture and anticoagulated in citrate phosphate dextrose solution from healthy human volunteers (males and females between the ages of 22 and 50). Human umbilical cord blood samples (20-70 ml) from healthy newborns (38-40 weeks gestational age, males and females) were collected in sterile syringes containing citrate phosphate dextrose solution as the anticoagulant. Written informed consent was obtained from all mothers before labor and delivery. The Institutional Review Board at the Indiana University School of Medicine approved all protocols.

Buffy Coat Cell Preparation

Human mononuclear cells (MNCs) were obtained from either adult peripheral or umbilical cord blood. Briefly, 20-100 ml of fresh blood was diluted one to one with Hanks Balanced Salt Solution (HBSS) (Invitrogen, Grand Island, N.Y.) and overlayed onto an equivalent volume of Ficoll-Paque (Amersham Biosciences) a ficoll density gradient material. Cells were centrifuged for 30 minutes at room temperature at 1800 rpms (740×g). MNCs were isolated and washed three times with EBM-2 medium (Cambrex, Walkersville, Md.) supplemented with 10-20% fetal bovine serum (Hyclone, Logan, Utah), 2% penicillin/streptomyocin (Invitrogen) and 0.25 µg/ml of amphotericin B (Invitrogen) (complete EGM-2 medium).

Culture and Quantitative Analysis of Endothelial Outgrowth Cells

Buffy coat MNCs were initially re-suspended in 12 ml of EGM-2 medium (Cambrex) supplemented with 10% fetal bovine serum, 2% penicillin/streptomyocin and 0.25 µg/ml of amphotericin B (complete EGM-2 medium). Four milliliters of cells were then seeded onto three separate wells of a six well tissue culture plate (BD Biosciences, Bedford Mass.) previously coated with extra cellular matrix proteins e.g. type I rat tail collagen (BD Biosciences) vitronectin, fibronectin, collagen type 10, polylysine. The plate was incubated at 37° C., 5% $CO_2$ in a humidified incubator. After 24 hours of culture, the non-adherent cells and debris were carefully aspirated, and the remaining adherent cells were washed one time with 2 ml of EGM-2 medium. After washing, 4 ml of EGM-2 medium was added to each well. EGM-2 medium was changed daily until day 7 of culture and then every other day until the first passage.

Figure 1A:
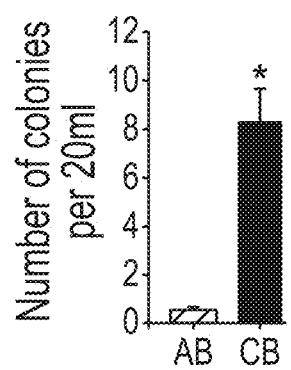
FIGS. 1A-1F. Isolation of endothelial progenitor cell colonies derived from adult peripheral and umbilical cord blood.
Figure 1B:
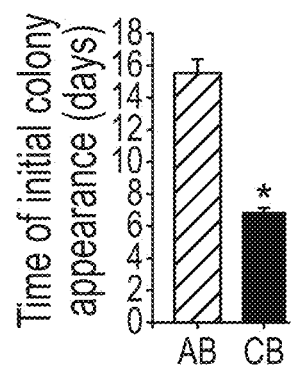
Figure 1C:
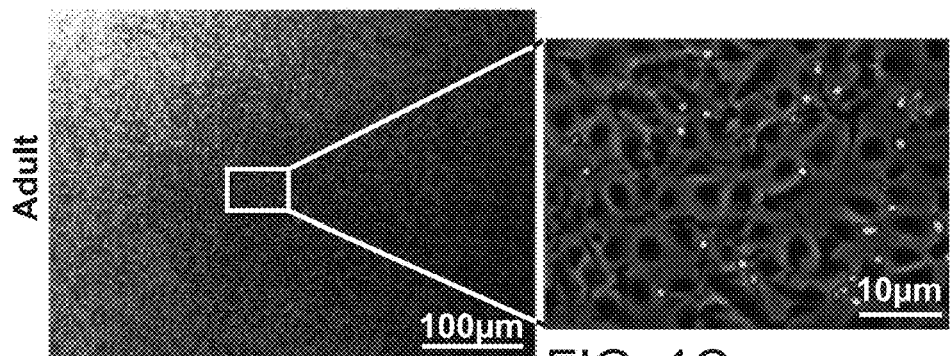
Figure 1D:
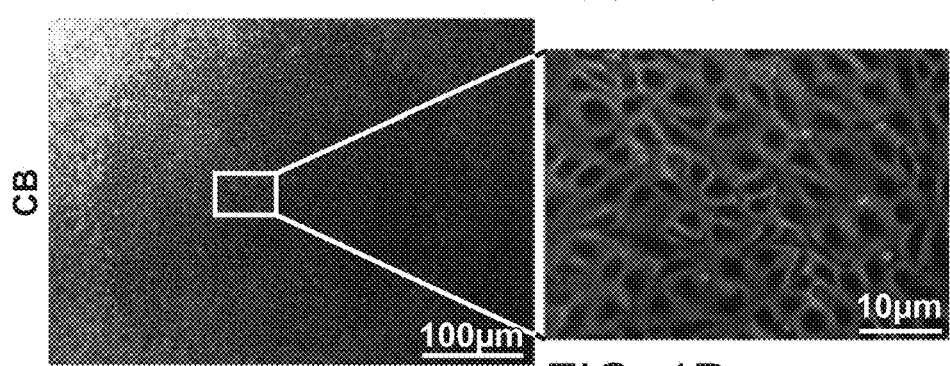
Figure 1E:
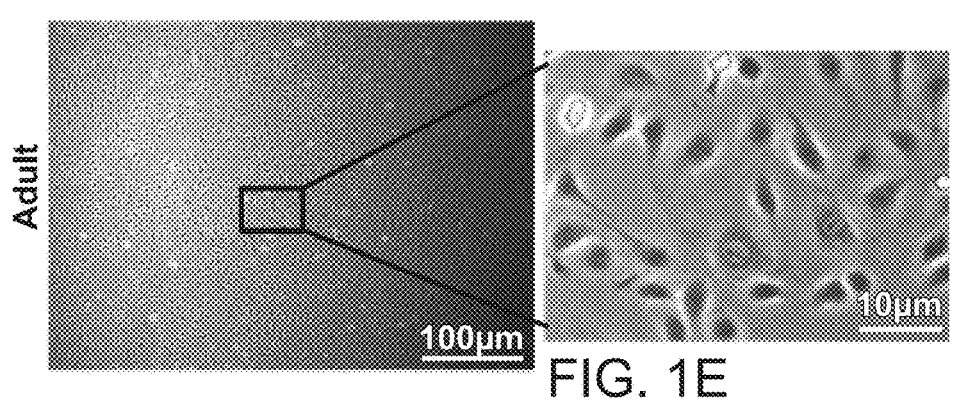
Figure 1F:
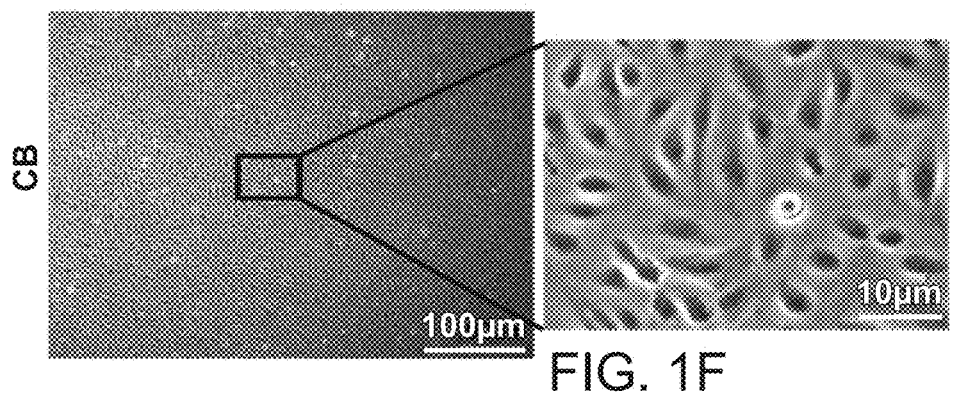

Colonies of cells initially appeared between 5 days and 22 days of culture and were identified as well circumscribed monolayers of cobblestone appearing cells (FIG. 1C). Colonies were enumerated by visual inspection using an inverted microscope at 40× magnification.

For passaging, cells were removed from the original collagen coated tissue culture plates using 0.05% trypsin-0.53 mM EDTA (Invitrogen), resuspended in 10 ml of EGM-2 media and plated onto 75 $cm^2$ tissue culture flasks coated with type I rat tail collagen. Monolayers of endothelial cells were subsequently passaged after becoming 90-100% confluent.

Culture of HUVECs and HAECs

Two approaches were used to directly isolate the endothelial cells from arterial or venous vessels. In the first approach, a 20 G blunt end needle was inserted into one end of an incised vessel and the vascular contents (plasma with blood cells) were flushed out the opposite end using sterile saline. Vascular clamps were then applied to isolate each end of the vessel (3-5 cm in length). A solution of 0.1% collagenase in Hanks balanced salt solution (HBSS) was injected through the vessel wall via a 23 G needle, and the vessel segments were incubated for 5 min at 37° C. The vascular clamp from one end of the vessel was then removed and the endothelial cells were expelled via infusion of a cell dissociation buffer (Gibco) (injected through the distal end of the vessel opposite the "open" end of the vessel). The vessel segments were infused with a minimum of 10 mL of cell dissociation buffer. The suspended cells were centrifuged at 350×g and washed in EBM-2 media with 10% FBS, counted, and viability checked using Trypan blue exclusion.

The second approach is best suited for large diameter vessels (>1 cm). The vessel was incised along the entire length and opened with the endothelial lumen exposed. Any remaining blood cells and plasma were washed away with HBSS. The endothelium was removed by firm scraping with a rubber policeman in a single end-to-end motion. The cells adhering to the rubber policemen were washed free by swirling the policemen in a solution of EBM-2 with 10% FBS in a 6 cm tissue culture well (precoated with extracellular matrix proteins). Cells were cultured with visual examination each day. Colonies of endothelium emerge in 3-10 days. The adherent endothelial colonies were removed by trypsin-EDTA and transferred to T 25 flasks that were coated with extracellular matrix proteins. Cryopreserved human umbilical vein endothelial cells (HUVECs) and human aortic endothelial cells (HAECs) were obtained from Cambrex at passage three. Cells were seeded in 75 $cm^2$ tissue culture flasks precoated with type I rat tail collagen in complete EGM-2 medium for passage.

Growth Kinetics and Estimate of Replicative Capacity of EPCs.

At the time of first passage cells were enumerated by a trypan blue exclusion assay (Sigma, St. Louis, Mo.). Monolayers of cells were then grown to 90% confluence and passaged. At each passage, cells were enumerated for calculation of a growth kinetic curve, population doubling times (PDTs), and cumulative population doubling levels (CPDLs).

The number of population doublings (PDs) occurring between passages was calculated according to the equation: $PD=\log_2(C_H/C_S)$ where $C_H$ is the number of viable cells at harvest and $C_S$ is the number of cells seeded. The sum of all previous PDs determined the CPDL at each passage. The PDT was derived using the time interval between cell seeding and harvest divided by the number of PDs for that passage.

MATRIGEL® Assays and Uptake of Acetylated-Low Density Lipoprotein (Ac-LDL or Dil-Ac-LDL)

MATRIGEL® (extracellular matrix proteins) assays were performed. Briefly, early passage (2-3) HPP-ECFC-derived or EPC-derived endothelial cells were seeded onto 96 well tissue culture plates previously coated with 30 μl of MATRIGEL® (extracellular matrix proteins) (BD Biosciences) at a cell density of 5000-20,000 cells per well. Cells were observed every two hours for capillary-like tube formation.

To assess the ability of attached HPP-ECFC and progeny or EPC and progeny to incorporate Ac-LDL or Dil-Ac-LDL), 10 μg/ml of Ac-LDL (Biomedical Technologies Inc., Stoughton, Mass.) was added to the media of cells cultured in a 6 well type I rat tail collagen coated tissue culture plate. Cells were incubated for 30 minutes or 4 hours at 37° C. and then washed three times with phosphate buffered saline (PBS) stained with 1.5 μg/ml of DAPI (Sigma) and examined for uptake of Ac-LDL or Dil-Ac-LDL by using a fluorescent microscope.

Immunophenotyping of Endothelial Cells by Fluorescence Cytometry

Early passage (1-2) or (3-4) HPP-ECFC and progeny or EPC and progeny ($5\times10^5$) were incubated at 4° C. for 30-60 minutes with varying concentrations of the primary or isotype control antibody as outlined below in 100 μl of PBS and 2% FBS. Cells were washed three times with PBS containing 2% FBS and analyzed by fluorescence activated cell sorting (FACS©) (Becton Dickinson, San Diego, Calif.). Directly conjugated primary murine monoclonal antibodies against human CD31 conjugated to fluorescein isothiocyanate (FITC) (BD Pharmingen, San Diego, Calif.) were used at a 1:20 dilution, human CD34 conjugated to allophycocyanin (APC) (BD Pharmingen) at a 1:25 dilution, human CD14 conjugated to FITC (BD Pharmingen) at a 1:10 dilution, human CD45 conjugated to FITC (BD Pharmingen) at a 1:10 dilution, human CD 117 conjugated to APC (BD Pharmingen) at a 1:100 dilution, human CD 146 conjugated to phycoerythrin (PE) (BD Pharmingen) at a 1:10 dilution, human AC133 conjugated to PE (Miltenyi Biotec, Auburn, Calif.) at a 1:5 dilution, human CD141 conjugated to FITC (Cymbus Biotechnology, Chandlers Ford, UK) at a 1:10 dilution, human CD 105 (BD Pharmingen) conjugated to Alexa Fluor 647 (Alexa Fluor 647 monoclonal antibody labeling kit, Molecular Probes, Eugene, Oreg.) at a 1:100 dilution, and human CD 144 conjugated to Alexa Fluor 647 at a 1:100 dilution.

To test for cell surface expression of vascular cell adhesion molecule (VCAM-1) after activation by a cell agonist, serum starved endothelial cells were stimulated with either 10 ng/ml of recombinant human interleukin one (IL-1) (Peprotech, Rocky Hill, N.J.) or 10 ng/ml of recombinant human tumor necrosis factor-alpha (TNF-α) (Peprotech) for 4 hours at 37° C. Following stimulation, cell surface expression of VCAM-1 was tested utilizing a primary antibody against human VCAM-1 conjugated to FITC (BD Pharmingen) at a 1:20 dilution. For all isotype controls for immunopherotyping and UCAM-1 expression, the following antibodies were used: mouse $IgG_{2a}$, κ, conjugated to FITC (BD Pharmingen), mouse $IgG_1$, κ conjugated to FITC (BD Pharmingen), mouse $IgG_1$, κ conjugated to PE (BD Pharmingen), and mouse $IgG_1$, κ conjugated to APC (BD Pharmingen).

For detection of cell surface expression of von Willebrand factor (vWF) and flk-1, cells were fixed in acetone for 10 minutes at room temperature, washed two times with PBS, and blocked and permeabilized for 30 minutes with PBS, 3% nonfat dry milk, and 0.1% Triton X-100 (Sigma). We used 2 μg/ml of a primary antibody directed against human vWF (Dako, Carpenteria, Calif.) and a biotinylated primary antibody directed against human flk-1 (Sigma) at a 1:20 dilution. The secondary antibody used for vWF was a goat anti-rabbit antibody conjugated to FITC (BD Pharmingen) at a 1:100 dilution and the secondary antibody used for flk-1 was strepavidin conjugated to APC (BD Pharmingen) at a 1:100 dilution. For the isotype control for vWF, we used rabbit Ig primary antibody (Dako) at a 1:100 dilution with anti-rabbit Ig secondary antibody conjugated to FITC (BD Pharmingen) at a 1:100 dilution. For the isotype control for flk-1, we used a biotinylated mouse $IgG_1$, κ (BD Pharmingen) primary antibody at a 1:100 dilution with a strepavidin APC secondary antibody (BD Pharmingen) at a 1:100 dilution.

Telomerase Activity Assay

For detection of telomerase activity, the telomeric repeat amplification protocol (TRAP) was employed in the form of a TRAP-eze telomerase detection kit (Oncor, Gaithersburg, Md.). Briefly, 1000 cultured HPP-ECFC or EPC colonies were absorbed onto filter papers and lysed in TRAP assay buffer. The lysed material was subjected to PCR amplification and the PCR products (6-bp incremental ladder) were electrophoresed on a non-denaturing polyacrylamide gel and visualized by DNA staining or radiolabeled with $^{32}P$. PCR products were loaded as neat or ⅒ or ¹⁄₁₀₀ dilutions and the level of intensity of staining compared to the HELA cell line (1000 cells) positive control.

Thymidine Incorporation Assays

Endothelial colony-derived endothelial cells were deprived of growth factors and cultured in EBM-2 media supplemented with 5% FBS for 24 hours. Next, $3\times10^4$ cells were plated in each well of 6-well tissue culture dishes pre-coated with type I collagen and cultured for 16 hours in EBM-2 media supplemented with 1% FBS. Cells were then cultured in EBM-2 without serum for an additional eight hours to ensure quiescence. Cells were stimulated in EBM-2 media supplemented with 10% FBS with 25 ng/ml of recombinant human vascular endothelial growth factor (rhVEGF) (Peprotech), 25 ng/ml of recombinant human basic fibroblast growth factor (rhbFGF) (Peprotech) or no growth factors, as indicated, in a 37° C., 5% $CO_2$, humidified incubator. Some cells were cultured in EBM-2 media without growth factors or FBS. Cells were cultured for 16 hours, and 1 µCi of tritiated thymidine (Perkin Elmer Life Sciences Products, Boston, Mass.) was added 5 hours prior to the harvest. Cells were lysed with 0.1 N sodium hydroxide for one hour. Lysates were collected into 5 ml of liquid scintilant (Fisher Scientific, St. Louis, Mo.) and β emission was measured. Assays were performed in triplicate.

Generation of GALV-Pseudotyped MFG-EGFP

The MFG-EGFP retrovirus vector expresses the enhanced green fluorescent protein (EGFP) under the control of the Moloney murine leukemia virus long terminal repeat (LTR) and has been previously described by Pollok et al. (2001). For generation of the GALV-pseudotyped vector, supernatant from an amphotrophic MFG-EGFP clone was used to infect the PG 13 packaging line (American Type Culture Collection (ATCC), Manassas, Va.), and infected cells were isolated by single cell cloning. Individual clones were screened for titer by infecting $5\times10^5$ human erythroleukemic cells (HEL) (ATCC) and determining the percent EGFP expression 48 hours after end-point dilution of supernatant. MFG-EGFP clone 5 has a titer of $0.5-1\times10^6$ infectious units/ml and was used for experiments.

Retroviral Transduction of Endothelial Cells

Early passage (1-2) endothelial colony-derived endothelial cells were transduced with equivalent starting titers of MGF-EGFP supernatant. Six well non-tissue culture plates were coated with 5 µg/cm² fibronectin CH-296 (Takara Shuzo, Otsu, Japan) for 2 hours at room temperature or overnight at 4° C. Plates were washed one time with PBS, and endothelial cells were plated at $5\times10^4$ cells/cm² for transduction. Cells were infected with retrovirus supernatant diluted 1:1 with complete EGM-2 for 4 hours on 2 consecutive days with a change of complete EGM-2 media for overnight incubation. After the second round of infection, cells were harvested, counted and analyzed for EGFP expression by fluorescence cytometry.

Single Cell Assays

Early passage (1-4) endothelial colony-derived endothelial cells, transduced with the MFG-EGFP retrovirus, were sorted by fluorescence cytometry for EGFP expression. A FACS Vantage Sorter (Becton Dickenson) was used (sort nozzle ≥100 microns at a sheath pressure of ≤9 pounds per square inch) to place one single endothelial cell expressing EGFP into each well of a 96 well flat bottom tissue culture plate pre-coated with type I collagen containing 20011 of complete EGM-2 media. Individual wells were examined under a fluorescence microscope at 50× magnification to ensure that only one cell had been placed into each well. Cells were cultured at 37° C., 5% $CO_2$ in a humidified incubator. Media was changed every four days by removing 100 µl and replacing it with 100 µl of fresh complete EGM-2 media. At day 14, each well was examined for the growth of endothelial cells from the single plated cell. To quantitate the frequency of dividing single endothelial cells, the number of wells, which had 2 or more endothelial cells with a fluorescent microscope at 100× magnification were counted. To enumerate the number of cells per well, the cells were counted by visual inspection with a fluorescent microscope at 100× magnification (less than 50 cells per well), or the cells were trypsinized and counted them with a hemacytometer utilizing a trypan blue exclusion assay (more than 50 cells per well).

The long term proliferative and replating potential of endothelial cells derived from a single cell was determined. At day 14 after initiation of culture, individual wells containing greater than 50 cells were trypsinized, collected in 500 µl of complete EGM-2 media and subcultured to a 24 well tissue culture dish coated with type I collagen. Four days after subculturing the cells, the media was aspirated and replaced with 500 µl of fresh complete EGM-2 media. On day 7, wells were examined for colony growth or cell confluence by visual inspection with a fluorescent microscope at 50× magnification. Cells were then trypsinized, counted, and subcultured in a 6 well tissue culture plate precoated with type I collagen. Following 7 days of culture in a six well plate, 10-12 wells, which contained confluent cell monolayers, for long-term cultures were selected under the conditions disclosed herein. For each sample, PDT and CPDL were calculated.

CD Markers

CD14 (lipopolysaccaride receptor)
CD31 (platelet endothelial cell adhesion molecule)
CD34 (sialomucin)
CD45 (common leukocyte antigen)
CD105 (endoglin)
CD 117 (c-Kit receptor)
CD133 (prominin 1)
CD141 (thrombomodulin)
CD144 (vascular endothelial cadherin)
CD146 (endothelial associated antigen, S-endo-1)
flk-1 (fetal liver kinase-1, receptor for vascular endothelial growth factor 2)

Confocal Imaging of EPC

Passage 3-5 EPC were grown in a T 75 flask for four days using EBM-2 media with 10% added FBS. When cells reached confluence, media was aspirated, 5 ml of sterile PBS was added to the flask, and then aspirated, trypsin—EDTA was added and the flask was incubated for 5 min at 37° C. To quench the trypsin, 5 mL of EBM-2 media with 10% FBS was added and the released EPC were centrifuged at 350×G for 10 min. The pelleted cells were washed with PBS and then resuspended in EBM-2 media with 10% FBS.

Glass chamber slides (4 chamber configuration; Corning) were coated with extracellular matrix proteins (e.g. collagen type 1 or 4, fibronectin, or vitronectin) over night at 4° C. and then washed with sterile PBS in the morning. The PBS was aspirated and cells in EBM-2 media with 10% FBS were added at 50 cells per chamber and incubated at 37° C. in 5% $CO_2$ for 7 days.

EPC containing slides were washed twice with PBS and cells were fixed in acetone for 10 min at room temperature, washed twice with PBS, and blocked and permeabilized for 30 minutes with PBS, 3% nonfat dry milk, and 0.1% Triton X100. To highlight the plasma membrane of the cells, a primary antibody to CD 146 conjugated to phycoerythrin (PE) was added (1.quadrature.g/mL) to the fixed cells along with 1.5 mg/mL DAPI for nuclear staining. After a 30 minute incubation, cells were washed twice in PBS and examined for fluorescence using a Zeiss 510 confocal microscope. An ultraviolet laser (351/364 nm excitation) and a helium-neon laser (543 nm excitation) were used to excite the DAPI and PE-labeled cells through a 40× water objective with the zoom kept on 0.7× magnification. Images were captured in a single plane and displayed as monochromatic images for presentation. NIH Image software was used to quantify the nuclear and cytoplasmic diameters of cells from various EPC colony types.

TABLE 1

Enumeration of the number and time of appearance of endothelial progenitor cell colonies isolated from adult peripheral and umbilical cord blood mononuclear cells.

| Adult peripheral blood | | | Umbilical Cord Blood | | |
|---|---|---|---|---|---|
| Donor | Number of Colonies/20 ml Blood | Day of First Colony | Donor | Number of Colonies/20 ml Blood | Day of First Colony |
| 1 | 0.50 | 15 | 1 | 8.18 | 7 |
| 2 | 0.83 | 17 | 2 | 5.45 | 6 |
| 3 | 0.35 | 13 | 3 | 13.97 | 7 |
| 4 | 0.83 | 21 | 4 | 4.92 | 7 |
| 5 | 0.58 | 13 | 5 | 9.79 | 7 |
| 6 | 0.17 | 22 | 6 | 1.14 | 8 |
| 7 | 0.00 | — | 7 | 4.09 | 10 |
| 8 | 0.60 | 14 | 8 | 9.55 | 6 |
| 9 | 1.00 | 18 | 9 | 11.33 | 6 |
| 10 | 0.40 | 17 | 10 | 0.67 | 6 |
| 11 | 0.60 | 14 | 11 | 16.00 | 5 |
| 12 | 0.60 | 17 | 12 | 6.00 | 7 |
| 13 | 0.00 | — | 13 | 16.00 | 6 |
| 14 | 0.33 | 12 | | | |
| 15 | 1.33 | 11 | | | |
| 16 | 0.67 | 13 | | | |
| 17 | 0.00 | — | | | |
| 18 | 1.00 | 16 | | | |

Co-Culture of HPP-ECFC and CD34+ Cells Expands NOD-SCID) Repopulating Cells.

Human CD34+ bone marrow cells, which have previously been shown to harbor marrow repopulating cells in NOD/SCID mice (SRCs) were isolated. Typically $0.5-1.0 \times 10^6$ human marrow CD34+ cells are injected into NOD/SCID mice in order to achieve a level of human CD45+ chimerism of 5-50%. Initially only $9 \times 10^3$ CD34+ cells were injected into NOD-SCID mice as a control on the day of harvest from human bone marrow. $9 \times 10^3$ CD34+ cells were cultured in the presence of SCF, G-CSF, TPO, and Flt-3 for seven days. These are the growth factors currently used to maximally expand HSCs ex vivo. $9 \times 10^3$ CD34+ cells were co-cultured with monolayers of cord blood HPP-ECFC derived progeny in the absence of growth factors for seven days. Following seven days of culture, the cultured CD34+ cells were injected into NOD-SCID mice and the peripheral blood of transplanted mice was tested for the presence of human cells four weeks after transplantation. Co-culture of CD34+ cells with growth factors for 7 days increased the percentage of human cells detected in NOD-SCID mice 8 weeks after transplantation 10 fold compared to CD34+ cells injected shortly after isolation from human bone marrow (FIG. 12A). Despite injecting a very limited number of cells compared to prior studies, co-culture of CD34+ cells with cord blood HPP-ECFC-derived cells increased the percentage of human cells detected in NOD-SCID mice 8 weeks after transplantation 260 fold (FIG. 12C). Both human myeloid and lymphoid lineages were detected eight weeks after transplantation indicating that multilineage reconstitution of the hematopoietic system was achieved with CD34+ cells co-cultured with cord blood HPP-ECFC.

Starting with 2 T75 flasks of confluent monolayers of HPP-ECFC-derived cells, cells were first washed with Hanks balanced salt solution without calcium or magnesium (HBBS), then 1.5 mL of Trypsin EDTA (Gibco) was added to each flask for 1 minute. Next 8.5 mL of endothelial basal medium 2 (EBM2) (Cambrex) with 10% fetal bovine serum (FBS) (Hyclone), was added and suspended cells were collected and counted via Trypan blue exclusion on a hemacytometer.

HPP-ECFC-derived cells were plated at $3 \times 10^5$ cells/well onto collagen 1 precoated 6 well tissue culture plates (BD Biosciences). Cells were cultured with endothelial growth medium 2 (EGM2) (Cambrex) supplemented with 10% FBS and cultured overnight. The following morning the confluent cell monolayers were washed with EBM2+10% FBS twice and then co-cultured with 9,000 $CD34^+CD38^{dim}Lin^-$ (CD4, 8, 11b, 14, 24, 31, 33, and glycophorin A) adult human bone marrow-derived cells collected by fluorescence activated cell sorting resuspended in 4 mL of EBM2+10% FBS+ human megakaryocyte growth derived factor (MGDF) (100 ng/mL), granulocyte colony stimulating factor (G-CSF) (100 ng/mL), and stem cell factor (SCF) (100 ng/mL), and flt-3 ligand (100 ng/mL). Cells were cultured in 37° C. 5% $CO_2$ humidified incubator for 7 days without disturbance. In some cultures the CD34+ cells were co-cultured with the HPP-ECFC in EBM2+10% FBS and no added growth factors.

A 5 mL pipette was used to aspirate the nonadherent cells and media (4 mL) at the end of the 7 day co-culture. Wells were washed once with 2 mL phosphate buffered saline (PBS) and the PBS with nonadherent cells added to the original aspirate. To the same wells, 1 mL of cell dissociation buffer (Gibco) was added for 4 minutes at room temperature, and then the cell dissociation buffer and loosened cells were titrated in the well gently before aspiration and adding to the original aspirate. Finally, the HPP-ECFC monolayers were washed one final time with 2 mL of PBS and this solution with scant cells was added to the original aspirate. The final volume of media and cells was 9 mL.

The cell suspension was centrifuged at 1500 rpm (514×g) at room temperature for 10 minutes. The solution was removed and the cell pellet was dislodged mechanically then resuspended in ½-1 mL of EBM2+10% FBS. Cells were counted in Trypan blue on a hemacytometer. Recovered cells were plated in progenitor assays or injected intravenously into NOD/SCID mice.

The method outlined above may be modified to provide a graft for a human transplant. In this instance, the HPP-ECFC progeny is plated in T75 flasks or in a perfusion chamber system to permit large numbers of CD34+ hematopoietic stem cells (autologous or allogeneic human cord blood-, mobilized peripheral blood-, or marrow-derived) to be expanded in the presence of the cord blood HPP-ECFC. Systems are used that will permit the donor CD34+ cells to be cultured with the HPP-ECFC progeny without the cells directly touching and, thus, the donor CD34+ cells can be expanded, recovered, and transplanted into the human patient without the donor cells being "contaminated" with the cord blood HPP-ECFC progeny.

DOCUMENTS

The following documents are incorporated by reference to the extent that methods and compositions disclosed are used in practice of the present invention.

Albella, B., J. Segovia, et al. (2003) "Ex vivo expansion of hematopoietic stem cells." Methods Mol. Biol. 215: 363-373.

Antonchuk, J., G. Sauvageau, et al. (2002) "HOXB4-Induced expansion of adult hematopoietic stem cells ex vivo." Cell 109: 39-45.

Asahara, T., Murohara, T., Sullivan, A., Silver, M., van der Zee, R., Li, T., Witzenbichler, B., Schatteman, G., and Isner, J. M. 1997. Isolation of putative progenitor endothelial cells for angiogenesis. Science 275:964-967.

Auerbach R, Lewis R, Shinners B, Kubai L, Akhtar N. 2003. Angiogenesis assays: a critical overview. Clin Chem. 49:32-40

Bailey, A. S., and Fleming, W. H. 2003. Converging roads: evidence for an adult hemangioblast. Exp Hematol 31:987-993.

Barker, J. E., S. Davies, et al. (2001) "Survival after transplantation of unrelated donor umbilical cord blood is comparable to that of human leukocyte antigen-matched unrelated bone marrow: results of a matched-pair analysis." Blood 97(10): 2957-2961.

Bompais, H., Chagraoui, J., Canron, X., Crisan, M., Liu, X. H., Anjo, A., Tolla-Le Port, C., Leboeuf, M., Charbord, P., Bikfalvi, A., et al. 2004. Human endothelial cells derived from circulating progenitors display specific functional properties compared with mature vessel wall endothelial cells. Blood 103:2577-2584.

Bornhauser, M. (2003). "Ex vivo expansion of umbilical cord blood cells on feeder layers." Methods Mol. Biol. 215: 341-349.

Brandt, J., A. Bartholomew, et al. (1999) "Ex vivo expansion of autologous bone marrow CD34(+) cells with porcine microvascular endothelial cells results in a graft capable of rescuing lethally irradiated baboons." Blood 94(1): 106-113.

Brandt, J., H. Galy, et al. (1998) "Bone marrow repopulation by human marrow stem cells after long-term expansion culture on a porcine endothelial cell line." Experimental Hematology 26: 950-961.

Broxmeyer, H. E., Douglas, G. W., Hangoc, G., Cooper, S., Bard, J., English, D., Amy, M., Thomas, L., and Boyse, E. A. 1989. Human umbilical cord blood as a potential source of transplantable hematopoietic stem/progenitor cells. Proc Natl Acad Sci US A 86:3828-3832.

Cairo, M. S., and Wagner, J. E. 1997. Placental and/or umbilical cord blood: an alternative source of hematopoietic stem cells for transplantation. Blood 90:4665-4678.

Choi, K., Kennedy, M., Kazarov, A., Papadimitriou, J. C., and Keller, G. 1998. A common precursor for hematopoietic and endothelial cells. Development 125:725-732.

Chute, J. P., A. A. Saini, et al. (2002) "Ex vivo culture with human brain endothelial cells increases the SCID-repopulating capacity of adult human bone marrow." Blood 100(13): 4433-9.

Devine, S., H. Lazarus, et al. (2003) "Clinical application of hematopoietic progenitor cell expansion: current status and future prospects." Bone Marrow Transplant 31(4): 241-252.

Gulati, R., Jevremovic, D., Peterson, T. E., Chatterjee, S., Shah, V., Vile, R. G., and Simari, R. D. 2003. Diverse origin and function of cells with endothelial phenotype obtained from adult human blood. Circ Res 93:1023-1025.

Heike, T. and T. Nakahata (2002) "Ex vivo expansion of hematopoietic stem cells by cytokines." Biochimica et Biophysica Acta 1592(3): 313-321.

Hristov, M., Erl, W., and Weber, P. C. 2003. Endothelial progenitor cells: mobilization, differentiation, and homing. Arterioscler Thromb Vasc Biol 23:1185-1189.

Hur, J., Yoon, C. H., Kim, H. S., Choi, J. H., Kang, H. J., Hwang, K. K., Oh, B. H., Lee, M. M., and Park, Y. B. 2004. Characterization of two types of endothelial progenitor cells and their different contributions to neovasculogenesis. Arterioscler Thromb Vasc Biol 24:288-293.

Ingram D A, Mead L E, Tanaka H, et al. 2004. Identification of a novel hierarchy of endothelial progenitor cells utilizing human peripheral and umbilical cord blood. Blood 104:2752-2760

Kalka, C., Masuda, H., Takahashi, T., Kalka-Moll, W. M., Silver, M., Kearney, M., Li, T., Isner, J. M., and Asahara, T. 2000. Transplantation of ex vivo expanded endothelial progenitor cells for therapeutic neovascularization. Proc Natl Acad Sci USA 97:3422-3427.

Kawamoto, A., Gwon, H. C., Iwaguro, H., Yamaguchi, J. I., Uchida, S., Masuda, H., Silver, M., Ma, H., Kearney, M., Isner, J. M., et al. 2001. Therapeutic potential of ex vivo expanded endothelial progenitor cells for myocardial ischemia. Circulation 103:634-637.

Kennedy, M., Firpo, M., Choi, K., Wall, C., Robertson, S., Kabrun, N., and Keller, G. 1997. A common precursor for primitive erythropoiesis and definitive haematopoiesis. Nature 386:488-493.

Kim, N. W., Piatyszek, M. A., Prowse, K. R., Harley, C. B., West, M. D., Ho, P. L., Coviello, G. M., Wright, W. E., Weinrich, S. L., and Shay, J. W. 1994. Specific association of human telomerase activity with immortal cells and cancer. Science 266:2011-2015.

Lacaud, G., Robertson, S., Palis, J., Kennedy, M., and Keller, G. 2001. Regulation of hemangioblast development. Ann NY Acad Sci 938:96-107; discussion 108.

Lewis, I. (2002) "Clinical and experimental uses of umbilical cord blood." Internal Medicine Journal 32: 601-609.

Lewis, I., G. Almeida-Porada, et al. (2001) "Umbilical cord blood cells capable of engrafting in primary, secondary, and tertiary xenogeneic hosts are preserved after ex vivo culture in noncontact system." Blood 97(3441-3449).

Lin, Y., Weisdorf, D. J., Solovey, A., and Hebbel, R. P. 2000. Origins of circulating endothelial cells and endothelial outgrowth from blood. J Clin Invest 105:71-77.

Little, M.-T. and R. Storb (2002) "History of haematopoietic stem-cell transplantation." Nat Rev Cancer 2: 231-238.

McNiece, I., G. Almeida-Porada, et al. (2002) "Ex vivo expanded cord blood cells provide rapid engraftment in sheep but lack long-term engrafting potential." Exp Hematol 30: 612-616.

McNiece, I. K., Stewart, F. M., Deacon, D. M., Temeles, D. S., Zsebo, K. M., Clark, S. C., and Quesenberry, P. J. 1989. Detection of a human CFC with a high proliferative potential. Blood 74:609-612.

McNiece, I. and R. Briddell (2001) "Ex Vivo expansion of hematopoietic progenitor cells and mature cells." Experimental Hematology 29: 3-11.

Murasawa, S., Llevadot, J., Silver, M., Isner, J. M., Losordo, D. W., and Asahara, T. 2002. Constitutive human telomerase reverse transcriptase expression enhances regenerative properties of endothelial progenitor cells. Circulation 106:1133-1139.

Murohara, T., H. Ikeda, et al. (2000) "Transplanted cord blood-derived endothelial precursor cells against postnatal neovascularization." The Journal of Clinical Investigation 105(11): 1527-1535.

Peichev, M., A. Maiyer, et al. (2000) "Expression of VEGFR-2 and AC133 be circulating human CD34(+) cells identifies a population of functional endothelial precursors." Blood 95:952-958.

Pollok, K. E., van Der Loo, J. C., Cooper, R. J., Hartwell, J. R., Miles, K. R., Breese, R., Williams, E. P., Montel, A., Seshadri, R., Hanenberg, H., et al., Differential transduc-

We claim:

1. A culture method for a high proliferative potential-endothelial colony forming cell (HPP-ECFC), the method comprising:
   (a) providing a blood sample selected from the group consisting of umbilical cord blood and blood vessel blood;
   (b) isolating a mononuclear cell from the blood sample;
   (c) seeding the mononuclear cell on a culture substrate, wherein the culture substrate comprises a coating comprising an extracellular matrix molecule (ECM);
   (d) culturing the seeded adherent mononuclear cell in a culture medium for about 5 to about 10 days to form a colony comprising cells;
   (e) immunophenotyping the cells from the colony to determine expression of CD31, CD141, CD105, CD146, CD144, vWF, and flk-1, but not CD45 and CD14; and
   (f) culturing the cells that express CD31, CD141, CD105, CD144, CD146, vWF, and flk-1, but do not express CD45 and CD14, wherein the cells have a nuclear diameter ranging from 8 microns to 10 microns.

2. The method of claim 1 further comprising subculturing the cells that express CD31, CD141, CD105, CD146, CD144, vWF, and flk-1, but not CD45 and CD14 for at least 30 population doublings.

3. The method of claim 1 further comprising subculturing a single cell that expresses CD31, CD141, CD105, CD146, CD144, vWF, and flk-1, but not CD45 and CD14 on an ECM coated plate to form a secondary colony comprising at least 2000 cells.

4. The method of claim 3, further comprising subculturing a single cell of the secondary colony on an ECM coated plate to form a tertiary colony.

5. The method of claim 1, wherein the culture medium comprises complete EGM-2 media.

6. The method of claim 1, wherein the extracellular matrix molecule is type I collagen.

7. The method of claim 1 further comprising analyzing the cells that express CD31, CD141, CD105, CD146, CD144, vWF, and flk-1, but not CD45 and CD14 for ingestion of acetylated-low density lipoprotein.

8. The method of claim 1, wherein the number of cells increases about $10^{20}$ fold over a period of 100 days in culture.

9. The method of claim 1, further comprising transducing the cells that express CD31, CD141, CD105, CD144, CD146, vWF, and flk-1, but do not express CD45 and CD14 with a nucleic acid encoding a marker.

10. The method of claim 9, wherein the marker is green fluorescent protein.

11. The method of claim 9, further comprising selecting a single cell expressing the nucleic acid encoding the marker.

12. The method of claim 11, wherein the single cell expressing the nucleic acid encoding the marker is plated.

13. The method of claim 12, wherein the single cell expressing the nucleic acid encoding the marker is plated by fluorescent cytometry sorting.

14. The method of claim 12, wherein the single cell expressing the nucleic acid encoding the marker forms a secondary colony comprising at least 2000 cells.

15. The method of claim 14, further comprising subculturing a single cell of the secondary colony on an ECM coated plate to form a tertiary colony.

* * * * *